(12) United States Patent
Jackson et al.

(10) Patent No.: US 12,410,385 B2
(45) Date of Patent: *Sep. 9, 2025

(54) AUTOMATIC DISHWASHING DETERGENT COMPOSITION COMPRISING AN AMYLASE

(71) Applicant: The Procter & Gamble Company, Cincinnati, OH (US)

(72) Inventors: Michelle Jackson, Newcastle upon Tyne (GB); Katarzyna Bell-Rusiewicz, Newcastle upon Tyne (GB); Manasi Bhate, San Francisco, CA (US); Hon Kit Chan, San Francisco, CA (US); Jonathan Lassila, South San Francisco, CA (US); Brian James Paul, Wilmington, DE (US); Sandra W. Ramer, Sunnyvale, CA (US); Patricia Tran, San Jose, CA (US)

(73) Assignee: The Procter & Gamble Company, Cincinnati, OH (US)

( * ) Notice: Subject to any disclaimer, the term of this patent is extended or adjusted under 35 U.S.C. 154(b) by 455 days.

This patent is subject to a terminal disclaimer.

(21) Appl. No.: 17/066,764

(22) Filed: Oct. 9, 2020

(65) Prior Publication Data
US 2021/0122998 A1    Apr. 29, 2021

Related U.S. Application Data

(60) Provisional application No. 62/925,252, filed on Oct. 24, 2019.

(51) Int. Cl.
| | |
|---|---|
| *C11D 3/386* | (2006.01) |
| *A47L 15/00* | (2006.01) |
| *C11D 3/395* | (2006.01) |
| *C12N 9/26* | (2006.01) |
| *C12N 9/28* | (2006.01) |
| *C12N 9/50* | (2006.01) |
| *C12N 9/54* | (2006.01) |

(52) U.S. Cl.
CPC ...... *C11D 3/38618* (2013.01); *A47L 15/0007* (2013.01); *C11D 3/3951* (2013.01); *C11D 3/3953* (2013.01); *C12N 9/2414* (2013.01); *C12Y 302/01001* (2013.01); *C11D 2111/14* (2024.01)

(58) Field of Classification Search
None
See application file for complete search history.

(56) References Cited

U.S. PATENT DOCUMENTS

| | | | | |
|---|---|---|---|---|
| 6,187,576 B1* | 2/2001 | Svendsen | ............ | C12N 9/2417 510/226 |
| 6,361,989 B1* | 3/2002 | Svendsen | ........... | C11D 3/38618 435/200 |
| 6,528,298 B1* | 3/2003 | Svendsen | ............... | C11D 3/386 536/23.7 |
| 9,856,437 B2 | 1/2018 | Andersen | | |
| 11,492,571 B2* | 11/2022 | Souter | .................. | C11D 3/3955 |
| 11,952,557 B2 | 4/2024 | Andersen | | |
| 2008/0193999 A1 | 8/2008 | Andersen | | |
| 2014/0287477 A1 | 9/2014 | Cascao-Pereira et al. | | |
| 2017/0121695 A1 | 5/2017 | Andersen et al. | | |
| 2018/0371441 A1 | 12/2018 | Regueira et al. | | |
| 2021/0171927 A1 | 6/2021 | Andersen et al. | | |
| 2021/0355470 A1 | 11/2021 | Kaasgaard | | |
| 2022/0364068 A1 | 11/2022 | Regueira et al. | | |

FOREIGN PATENT DOCUMENTS

| | | | | |
|---|---|---|---|---|
| JP | 2005239809 A | 9/2005 | | |
| WO | 9623873 A1 | 8/1996 | | |
| WO | 0164852 A1 | 9/2001 | | |
| WO | 2001064852 A1 | 9/2001 | | |
| WO | 2006002643 A2 | 1/2006 | | |
| WO | 2010115021 A3 | 12/2010 | | |
| WO | 2011076897 A1 | 6/2011 | | |
| WO | WO-2013063460 A2 * | 5/2013 | ............. | A21D 8/042 |
| WO | 2013063460 A3 | 6/2013 | | |
| WO | 2015044448 A1 | 4/2015 | | |
| WO | 2015189371 A1 | 12/2015 | | |
| WO | WO-2016126569 A1 * | 8/2016 | ........... | C11D 17/045 |
| WO | 2016203064 A2 | 12/2016 | | |
| WO | 2018184004 A1 | 10/2018 | | |
| WO | 2018224544 A1 | 12/2018 | | |

OTHER PUBLICATIONS

Singh et al., Curr. Protein Pept. Sci. 18:1-11, 2017 (Year: 2017).*
Zhang et al., Structure 26:1474-1485, 2018 (Year: 2018).*
PCT Search Report and Written Opinion for PCT/US2020/070673 dated Apr. 7, 2021, 17 pages.

* cited by examiner

*Primary Examiner* — David Steadman
(74) *Attorney, Agent, or Firm* — Elizabeth A. Conklin; George H. Leal; Carolyn S. Powell

(57) ABSTRACT

An automatic dishwashing cleaning composition comprising a variant α-amylase wherein the variant α-amylase comprises amino acid substitution(s) selected from the group consisting of:

i) a mutation at position 91 and one or more mutation(s) at an amino acid residue at the base of the α-amylase TIM barrel structure, defined as residues 6, 7, 40, 96, 98, 100, 229, 230, 231, 262, 263, 285, 286, 287, 288, 322, 323, 324, 325, 362, 363 and 364; and/or ii) a mutation at position 172 and a mutation in position 288 or 324; and/or iii) Y364L referring to SEQ ID NO: 1 for numbering.

20 Claims, No Drawings
Specification includes a Sequence Listing.

SEQUENCE LISTING

<160> NUMBER OF SEQ ID NOS: 6

<210> SEQ ID NO 1
<211> LENGTH: 486
<212> TYPE: PRT
<213> ORGANISM: Bacillus sp.

<400> SEQUENCE: 1

```
His His Asn Gly Thr Asn Gly Thr Met Met Gln Tyr Phe Glu Trp His
  1               5                  10                  15

Leu Pro Asn Asp Gly Gln His Trp Asn Arg Leu Arg Asn Asp Ala Ala
             20                  25                  30

Asn Leu Lys Asn Leu Gly Ile Thr Ala Val Trp Ile Pro Pro Ala Trp
         35                  40                  45

Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Ile Arg Thr Lys Tyr Gly
 65                  70                  75                  80

Thr Arg Ser Gln Leu Gln Ser Ala Ile Ala Ser Leu Gln Asn Asn Gly
                 85                  90                  95

Ile Gln Val Tyr Gly Asp Val Val Met Asn His Lys Gly Gly Ala Asp
            100                 105                 110

Gly Thr Glu Trp Val Gln Ala Val Glu Val Asn Pro Ser Asn Arg Asn
        115                 120                 125

Gln Glu Val Thr Gly Glu Tyr Thr Ile Glu Ala Trp Thr Lys Phe Asp
    130                 135                 140

Phe Pro Gly Arg Gly Asn Thr His Ser Ser Phe Lys Trp Arg Trp Tyr
145                 150                 155                 160

His Phe Asp Gly Thr Asp Trp Asp Gln Ser Arg Gln Leu Asn Asn Arg
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Arg Arg Trp Gly Val Trp Tyr
    210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Asn His Val Arg Ser Thr
                245                 250                 255

Thr Gly Lys Asn Asn Met Phe Ala Val Ala Glu Phe Trp Lys Asn Asp
            260                 265                 270

Leu Gly Ala Ile Glu Asn Tyr Leu His Lys Thr Asn Trp Asn His Ser
        275                 280                 285

Val Phe Asp Val Pro Leu His Tyr Asn Leu Tyr Asn Ala Ser Lys Ser
    290                 295                 300

Gly Gly Asn Tyr Asp Met Arg Gln Ile Leu Asn Gly Thr Val Val Ser
305                 310                 315                 320

Lys His Pro Ile His Ala Val Thr Phe Val Asp Asn His Asp Ser Gln
                325                 330                 335

Pro Ala Glu Ala Leu Glu Ser Phe Val Glu Ala Trp Phe Lys Pro Leu
            340                 345                 350

Ala Tyr Ala Leu Ile Leu Thr Arg Glu Gln Gly Tyr Pro Ser Val Phe
        355                 360                 365
```

```
Tyr Gly Asp Tyr Tyr Gly Ile Pro Thr His Gly Val Ala Ala Met Lys
    370             375                 380

Gly Lys Ile Asp Pro Ile Leu Glu Ala Arg Gln Lys Tyr Ala Tyr Gly
385             390                 395                 400

Thr Gln His Asp Tyr Leu Asp His His Asn Ile Ile Gly Trp Thr Arg
                405                 410                 415

Glu Gly Asn Ser Ala His Pro Asn Ser Gly Leu Ala Thr Ile Met Ser
            420                 425                 430

Asp Gly Pro Gly Gly Ser Lys Trp Met Tyr Val Gly Arg His Lys Ala
            435                 440                 445

Gly Gln Val Trp Arg Asp Ile Thr Gly Asn Arg Thr Gly Thr Val Thr
450                 455                 460

Ile Asn Ala Asp Gly Trp Gly Asn Phe Ser Val Asn Gly Gly Ser Val
465                 470                 475                 480

Ser Ile Trp Val Asn Lys
                485

<210> SEQ ID NO 2
<211> LENGTH: 485
<212> TYPE: PRT
<213> ORGANISM: Bacillus sp.

<400> SEQUENCE: 2

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
                20                  25                  30

Asn Leu Lys Ser Lys Gly Ile Thr Ala Val Trp Ile Pro Pro Ala Trp
            35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255
```

```
Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
            275                 280                 285

Phe Asp Val Pro Leu His Tyr Asn Leu Tyr Asn Ala Ser Lys Ser Gly
            290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
            435                 440                 445

Gln Val Trp Ser Asp Ile Thr Gly Asn Arg Thr Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 3
<211> LENGTH: 485
<212> TYPE: PRT
<213> ORGANISM: Bacillus sp.

<400> SEQUENCE: 3

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Ser Ala Val Trp Ile Pro Pro Ala Trp
            35                  40                  45

Lys Gly Ala Ser Gln Asn Asp Val Gly Tyr Gly Ala Tyr Asp Leu Tyr
            50                  55                  60

Asp Leu Gly Glu Phe Asn Gln Lys Gly Thr Ile Arg Thr Lys Tyr Gly
65                  70                  75                  80

Thr Arg Asn Gln Leu Gln Ala Ala Val Asn Ala Leu Lys Ser Asn Gly
            85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
            115                 120                 125
```

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
            165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
            245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
            275                 280                 285

Phe Asp Val Pro Leu His Tyr Asn Leu Tyr Asn Ala Ser Lys Ser Gly
            290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
            325                 330                 335

Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
            355                 360                 365

Gly Asp Tyr Tyr Gly Ile Pro Thr His Gly Val Pro Ala Met Lys Ser
370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
            405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
            435                 440                 445

Gln Val Trp Thr Asp Ile Thr Gly Asn Arg Ala Gly Thr Val Thr Ile
            450                 455                 460

Asn Ala Asp Gly Trp Gly Asn Phe Ser Val Asn Gly Gly Ser Val Ser
465                 470                 475                 480

Ile Trp Val Asn Lys
            485

<210> SEQ ID NO 4
<211> LENGTH: 485
<212> TYPE: PRT
<213> ORGANISM: Bacillus sp.

-continued

```
<400> SEQUENCE: 4

His His Asp Gly Thr Asn Gly Thr Ile Met Gln Tyr Phe Glu Trp Asn
1               5                   10                  15

Val Pro Asn Asp Gly Gln His Trp Asn Arg Leu His Asn Asn Ala Gln
            20                  25                  30

Asn Leu Lys Asn Ala Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Lys Ala Glu Leu Glu Arg Ala Ile Arg Ser Leu Lys Ala Asn Gly
                85                  90                  95

Ile Gln Val Tyr Gly Asp Val Val Met Asn His Lys Gly Gly Ala Asp
            100                 105                 110

Phe Thr Glu Arg Val Gln Ala Val Glu Val Asn Pro Gly Asn Arg Asn
        115                 120                 125

Gln Glu Val Ser Gly Thr Tyr Gln Ile Glu Ala Trp Thr Gly Phe Asn
    130                 135                 140

Phe Pro Gly Arg Gly Asn Gln His Ser Ser Phe Lys Trp Arg Trp Tyr
145                 150                 155                 160

His Phe Asp Gly Thr Asp Trp Asp Gln Ser Arg Gln Leu Ala Asn Arg
                165                 170                 175

Ile Tyr Lys Phe Arg Gly Asp Gly Lys Ala Trp Asp Trp Glu Val Asp
            180                 185                 190

Thr Glu Asn Gly Asn Tyr Asp Tyr Leu Met Tyr Ala Asp Val Asp Met
        195                 200                 205

Asp His Pro Glu Val Ile Asn Glu Leu Asn Arg Trp Gly Val Trp Tyr
    210                 215                 220

Ala Asn Thr Leu Asn Leu Asp Gly Phe Arg Leu Asp Ala Val Lys His
225                 230                 235                 240

Ile Lys Phe Ser Phe Met Arg Asp Trp Leu Gly His Val Arg Gly Gln
                245                 250                 255

Thr Gly Lys Asn Leu Phe Ala Val Ala Glu Tyr Trp Lys Asn Asp Leu
            260                 265                 270

Gly Ala Leu Glu Asn Tyr Leu Ser Lys Thr Asn Trp Thr Met Ser Ala
        275                 280                 285

Phe Asp Val Pro Leu His Tyr Asn Leu Tyr Gln Ala Ser Asn Ser Ser
    290                 295                 300

Gly Asn Tyr Asp Met Arg Asn Leu Leu Asn Gly Thr Leu Val Gln Arg
305                 310                 315                 320

His Pro Ser His Ala Val Thr Phe Val Asp Asn His Asp Thr Gln Pro
                325                 330                 335

Gly Glu Ala Leu Glu Ser Phe Val Gln Gly Trp Phe Lys Pro Leu Ala
            340                 345                 350

Tyr Ala Thr Ile Leu Thr Arg Glu Gln Gly Tyr Pro Gln Val Phe Tyr
        355                 360                 365

Gly Asp Tyr Tyr Gly Ile Pro Ser Asp Gly Val Pro Ser Tyr Arg Gln
    370                 375                 380

Gln Ile Asp Pro Leu Leu Lys Ala Arg Gln Gln Tyr Ala Tyr Gly Arg
385                 390                 395                 400
```

```
Gln His Asp Tyr Phe Asp His Trp Asp Val Ile Gly Trp Thr Arg Glu
                405                 410                 415
Gly Asn Ala Ser His Pro Asn Ser Gly Leu Ala Thr Ile Met Ser Asp
            420                 425                 430
Gly Pro Gly Gly Ser Lys Trp Met Tyr Val Gly Arg Gln Lys Ala Gly
        435                 440                 445
Glu Val Trp His Asp Met Thr Gly Asn Arg Ser Gly Thr Val Thr Ile
    450                 455                 460
Asn Gln Asp Gly Trp Gly His Phe Phe Val Asn Gly Gly Ser Val Ser
465                 470                 475                 480
Val Trp Val Lys Arg
                485

<210> SEQ ID NO 5
<211> LENGTH: 269
<212> TYPE: PRT
<213> ORGANISM: Bacillus sp.

<400> SEQUENCE: 5

Gln Gln Thr Val Pro Trp Gly Ile Thr Arg Val Gln Ala Pro Ala Val
1               5                   10                  15
His Asn Arg Gly Ile Thr Gly Ser Gly Val Arg Val Ala Ile Leu Asp
            20                  25                  30
Ser Gly Ile Ser Ala His Ser Asp Leu Asn Ile Arg Gly Gly Ala Ser
        35                  40                  45
Phe Val Pro Gly Glu Pro Thr Thr Ala Asp Leu Asn Gly His Gly Thr
    50                  55                  60
His Val Ala Gly Thr Val Ala Ala Leu Asn Asn Ser Ile Gly Val Ile
65                  70                  75                  80
Gly Val Ala Pro Asn Ala Glu Leu Tyr Ala Val Lys Val Leu Gly Ala
                85                  90                  95
Asn Gly Ser Gly Ser Val Ser Gly Ile Ala Gln Gly Leu Glu Trp Ala
            100                 105                 110
Ala Thr Asn Asn Met His Ile Ala Asn Met Ser Leu Gly Ser Asp Phe
        115                 120                 125
Pro Ser Ser Thr Leu Glu Arg Ala Val Asn Tyr Ala Thr Ser Arg Asp
    130                 135                 140
Val Leu Val Ile Ala Ala Thr Gly Asn Asn Gly Ser Gly Ser Val Gly
145                 150                 155                 160
Tyr Pro Ala Arg Tyr Ala Asn Ala Met Ala Val Gly Ala Thr Asp Gln
                165                 170                 175
Asn Asn Arg Arg Ala Asn Phe Ser Gln Tyr Gly Thr Gly Ile Asp Ile
            180                 185                 190
Val Ala Pro Gly Val Asn Val Gln Ser Thr Tyr Pro Gly Asn Arg Tyr
        195                 200                 205
Val Ser Met Asn Gly Thr Ser Met Ala Thr Pro His Val Ala Gly Ala
    210                 215                 220
Ala Ala Leu Val Lys Gln Arg Tyr Pro Ser Trp Asn Ala Thr Gln Ile
225                 230                 235                 240
Arg Asn His Leu Lys Asn Thr Ala Thr Asn Leu Gly Asn Ser Ser Gln
                245                 250                 255
Phe Gly Ser Gly Leu Val Asn Ala Glu Ala Ala Thr Arg
            260                 265
```

```
<210> SEQ ID NO 6
<211> LENGTH: 269
<212> TYPE: PRT
<213> ORGANISM: Bacillus sp.

<400> SEQUENCE: 6

Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
            130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
            195                 200                 205

Ala Ser Leu Asn Gly Thr Ser Met Ala Thr Pro His Val Ala Gly Ala
        210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

AUTOMATIC DISHWASHING DETERGENT COMPOSITION COMPRISING AN AMYLASE

PARTIES OF JOINT RESEARCH AGREEMENT

The claimed subject matter of the present application was made by or on behalf of the below parties to a joint research agreement. The joint research agreement was in effect on or before the date the claimed invention was made and the claimed invention was made as a result of activities undertaken with the scope of the joint research agreement. The parties to the joint research agreement are The Procter & Gamble Company and Danisco. Incorporated herein by reference is the ASCII text file of a sequence listing filed on Oct. 9, 2020, titled "CM5145_Sequence.txt," having the size of 22000 bytes and created on Oct. 21, 2019.

FIELD OF THE INVENTION

The present invention is in the field of detergents. In particular, it relates to an automatic dishwashing detergent composition comprising a new amylase. The composition provides improved cleaning versus compositions comprising conventional amylases.

BACKGROUND OF INVENTION

There is a permanent desire to improve the performance of automatic dishwashing. Amylases are important ingredients in automatic dishwashing compositions. When designing an amylase for automatic dishwashing several criteria need to be fulfilled. It should be stable in the detergent matrix prior to usage, it should be stable during wash and it should be highly active and fast to act during wash.

The object of the present invention is to provide a more stable automatic dishwashing composition that provide better cleaning and that performs better at both long hot cycles and short cycles.

SUMMARY OF THE INVENTION

According to the first aspect of the present invention, there is provided an automatic dishwashing cleaning composition. The composition comprises a specific amylase. The composition presents improved performance in hot cycles (the was temperature is above 40° C., preferably above 45° C.), long cycles (the main wash is longer than 15 mins) and short cycles (the main wash lasts less than 15 mins, preferably less than 12 minutes and especially less than 10 minutes) even when the dishware is heavily soiled.

The automatic dishwashing cleaning composition of the invention comprises a variant α-amylase wherein the variant α-amylase comprises amino acid substitution(s) selected from the group consisting of:
  i) a mutation at position 91 and one or more mutation(s) at an amino acid residue at the base of the α-amylase TIM barrel structure, defined as residues 6, 7, 40, 96, 98, 100, 229, 230, 231, 262, 263, 285, 286, 287, 288, 322, 323, 324, 325, 362, 363 and 364; and/or
  ii) a mutation at position 172 and a mutation in position 288 or 324; and/or
  iii) Y364L
referring to SEQ ID NO: 1 for numbering.

1. The α-amylase variant of the composition of the invention comprises a mutation at position 91 and/or a mutation at an amino acid residue at the base of the α-amylase TIM barrel structure, defined as residues 6, 7, 40, 96, 98, 100, 229, 230, 231, 262, 263, 285, 286, 287, 288, 322, 323, 324, 325, 362, 363 and 364, referring to SEQ ID NO: 1 for numbering.

2. Preferably, the mutation at position 91 is substitution of the naturally-present residue to a positively-charged residue.

3. Preferably, the mutation at position 91 is substitution of the naturally-present residue to arginine (i.e., X91R).

4. Preferably, the variant α-amylase of any of paragraphs 1-3, the at least one mutation at the base of the α-amylase TIM barrel structure is selected from the group consisting of X40N, X40D, X100F, X100L, X263Y, X288D, X288K, X288Q, X324R, X324N, X324M, X364L and X364M, more preferably from the group consisting of T40N, T40D, Y100F, Y100L, F263Y, S288D, S288K, S288Q, I324R, I324N, I324M, Y364L and Y364M.

5. Preferably, the α-amylase variant comprises an arginine at position 91 and at least one of the following features not present in naturally-occurring α-amylase: N or D at position 40, F or L at position 100, Y at position 263, D, K or Q at position 288, R, N or M at position 324 or L or M at position 364.

6. Preferably, the variant α-amylase of any of paragraphs 1-5 further comprises a mutation at a residue in the loop comprising surface-exposed residues 167, 169, 171, 172 and 176, referring to SEQ ID NO: 1 for numbering, more preferably from the group consisting of X167F, X169H, X171Y, X172R, X172N and X176S more preferably from the group consisting of W167F, Q169H, R171Y, Q172R, Q172N and R176S.

7. Preferably, the variant α-amylase of any of paragraphs 1-6 further comprises F at position 167, H at position 169, Y at position 171, R or N at position 172 or S at position 176, referring to SEQ ID NO: 1 for numbering.

8. Preferably, the variant α-amylase comprises a mutation at position 172 and a mutation at position 288, referring to SEQ ID NO: 1 for numbering, more preferably arginine or asparagine at position 172 and aspartic acid at position 288, referring to SEQ ID NO: 1 for numbering.

9. Preferably, the variant α-amylase of any of paragraphs 1-8 further comprises a mutation at position 116 and/or 281, referring to SEQ ID NO: 1 for numbering, more preferably arginine at position 116 or serine at position 281, referring to SEQ ID NO: 1 for numbering.

10. Preferably, the variant α-amylase of any of any of paragraphs 1-9 further comprises a mutation at position 190 and/or 244, referring to SEQ ID NO: 1 for numbering, more preferably proline at position 190 is and/or alanine, glutamic acid or glutamine at position 244, referring to SEQ ID NO: 1 for numbering.

11. Preferably, the variant α-amylase of any of paragraphs 1-10 further comprises deletion of at least two residues equivalent to R181, G182, T183, and G184, using SEQ ID NO: 1, more preferably pairwise deletions of residues equivalent to R181 and G182 or to residues T183 and G184.

12. Preferably the variant α-amylase is provided, comprising:
  (i) substitutions selected from the group consisting of:
    (a) X40N-X91R-X169H-X183M-X281N,
    (b) X172R-X190P-X288D,
    (c) X172R-X244E-X288D-X474R,
    (d) X91R-X172R-X190P-X324M,
    (e) X40N-X91R-X190P-X263Y,
    (f) X40N-X91R-X244E-X364L,
    (g) X91R-X172R-X190P-X324R,
    (h) X91R-X116R-X172R-X244E-X281S-X288D,
    (i)      X40N-X91R-X100E-X116R-X172N-X244Q-X281S, (j) X40N-X91R-X172R-X244Q-X263Y-X281S,
(k) X91R-X172R-X190P-X324N,
(l) X40D-X91R-X172R-X190P-X281S-X324R, and
(m) X364L; and
(ii) pairwise deletions of residues selected from the group consisting of residues equivalent to:
181 and 182, and
183 and 184,
using SEQ ID NO: 1 for numbering.

13. Preferably, the variant α-amylase of paragraph 12 comprises:
(i) substitutions selected from the group consisting of:
(a) T40N-S91R-Q169H-T183M-H281N,
(b) Q172R-E190P-S288D,
(c) Q172R-S244E-S288D-S474R,
(d) S91R-Q172R-E190P-I324M,
(e) T40N-S91R-E190P-F263Y,
(f) T40N-S91R-S244E-Y364L,
(g) S91R-Q172R-E190P-I324R,
(h) S91R-W116R-Q172R-S244E-H281S-S288D,
(i) T40N-S91R-Y100E-W116R-Q172N-S244Q-H281S,
(j) T40N-S91R-Q172R-S244Q-F263Y-H281S,
(k) S91R-Q172R-E190P-I324N,
(l) T40D-S91R-Q172R-E190P-H281S-I324R, and
(m) Y364L; and
(ii) pairwise deletions of residues selected from the group consisting of:
R181 and G182, and
T183 and G184,
using SEQ ID NO: 1 for numbering.

14. Preferably, the variant α-amylase comprises three or more of the following features: (a) D or N at position 40 and/or R at position 91 and (b) F at position 100, Y at position 263, D at position 288, M, N or R at position 324 and/or L at position 364, optionally in combination with (c) H at position 169, M at position 183M, N or S at position 281, N or R at position 172, P at position 190, E, Q or R at position 244, R at position 474, R at position 116, optionally in combination with pairwise deletions at positions 181 and 182 or 183 and 184, in all cases using SEQ ID NO: 1 for numbering.

15. Preferably, the variant α-amylase of any of paragraphs 1-14 has at least 70%, at least 80%, at least 90% or at least 95% amino acid sequence identity to the amino acid sequence of SEQ ID NO: 1, SEQ ID NO: 2, SEQ ID NO: 3 or SEQ ID NO: 4. Preferably, the composition of the invention further comprises a protease. The protease has at least 90%, preferably at least 95%, more preferably at least 98% and especially at least 99% identity with the amino acid sequence of SEQ ID NO:6 and wherein the protease comprises one or more, or two or more or three or more amino acid substitutions selected from the group consisting of:

S3V, S9R, A13V, A15T, G20*, L21F, I35V, N60D, V66A, N74D, S85N/R, S97SE, S97AD, S97D/G, S99G/M/D/E, S101A, V102E/I, G116V/R, S126F/L, P127Q, S128A, S154D, G157S, Y161A, R164S, A188P, V199I, Q200C/E/I/K/T/V/W/L, Y203W, N212D, M216S/F, A222V, Q239R/F, T249R, N255D and L256E,N,Q,D Preferably, the composition of the invention further comprises a protease wherein the protease has at least 80%, preferably at least 85%, more preferably at least 90% and especially at least 96% identity with the amino acid sequence of SEQ ID NO:5 or with the amino acid sequence of SEQ ID NO:6 and wherein the protease comprises amino acid substitutions selected from the group consisting of:

(i) at least one or two amino acid substitutions selected from the group consisting of: X198G/A/K/L/Q/R/T/V/S/L, X207Q, X211Q/N and X212Q in combination with at least one, two or three amino acid substitutions selected from the group consisting of: X039E, X074D, X099R, X126A, X127E and X128G; or
(ii) X039E-X074D-X099R-X116R-X126A-X127E-X128G-X211Q; X039E-X074D-X099R-X126A-X127E-X128G-X211N; X039E-X074D-X099R-X126A-X127E-X128G-X211Q; X039E-X074D-X099R-X126A-X127E-X128G-X207Q; or
(iii) any of the proteases of (i) and (ii) further comprising at least one amino acid substitution selected from X242D and X256E; or
(iv) X039E-X074D-X099R-X126A-X127E-X128G-X256E; using the SEQ ID NO:6 numbering.

According to a second aspect of the invention, there is provided a method of automatic dishwashing in hot long cycles.

The disclosure of the first aspect of the invention applies mutatis mutandis to the second aspect of the invention.

DETAILED DESCRIPTION OF THE INVENTION

The present invention encompasses an automatic dishwashing cleaning composition. The composition comprises a new amylase. The composition provides good cleaning under a wide range of dishwashing programs.

By "hot" cycle is herein understood a dishwashing program in which the main cycle is performed at a temperature above 40° C., preferably above 45° C.

By "long" cycle is herein understood a dishwashing program in which the main cycle has a duration of at least 15, preferably at least 20 and more preferably at least 25 minutes.

By "short" cycle is herein understood a dishwashing program in which the main cycle has a duration of less than 15, preferably less than 12, preferably less than 10 minutes.

The Amylase of the Invention

The composition of the invention comprises a variant α-amylase, the variant α-amylases preferably have a defined percentage of identity with respect to a reference α-amylase (α-amylases of SEQ ID NO: 1 to 4).

The variant α-amylase of the composition of the invention is herein sometimes referred to as "the amylase of the invention". The amylases having any of sequences ID NO:1 to 4 are herein sometimes referred to as "the reference amylase" or "the parent amylase". The relatedness between two amino acid sequences or between two nucleotide sequences is described by the parameter "sequence identity".

The term "variant" means an amylase comprising a mutation, i.e., a substitution, insertion, and/or deletion, at one or more (e.g., several) positions relative to the reference amylase. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 80%, preferably at least 85%, more preferably a least 90% and especially 96% identity with the reference protease.

The composition of the invention comprises combinatorial variants of maltopentaose/maltohexaose-forming α-amylases that show a high degree of performance in automatic dishwashing applications. The variants are most closely related to an α-amylase from a *Bacillus* sp., herein, referred to as AA2560, and previously identified as BspAmy24 (SEQ ID NO: 1) in WO 2018/184004. The mature amino acid sequence of AA2560 α-amylase is shown, below, as SEQ ID NO: 1:

```
HHNGTNGTMM QYFEWHLPND GQHWNRLRND AANLKNLGIT

AVWIPPAWKG TSQNDVGYGA YDLYDLGEFN QKGTIRTKYG

TRSQLQSAIA SLQNNGIQVY GDVVMNHKGG ADGTEWVQAV

EVNPSNRNQE VTGEYTIEAW TKFDFPGRGN THSSFKWRWY

HFDGTDWDQS RQLNNRIYKF RGTGKAWDWE VDTENGNYDY

LMYADVDMDH PEVINELRRW GVWYTNTLNL DGFRIDAVKH

IKYSFTRDWL NHVRSTTGKN NMFAVAEFWK NDLGAIENYL

HKTNWNHSVF DVPLHYNLYN ASKSGGNYDM RQILNGTVVS

KHPIHAVTFV DNHDSQPAEA LESFVEAWFK PLAYALILTR

EQGYPSVFYG DYYGIPTHGV AAMKGKIDPI LEARQKYAYG

TQHDYLDHHN IIGWTREGNS AHPNSGLATI MSDGPGGSKW

MYVGRHKAGQ VWRDITGNRT GTVTINADGW GNFSVNGGSV

SIWVNK
```

A closely related maltopentaose/maltohexaose-forming α-amylase is from *Bacillus* sp. 707, herein, referred to as "AA707." The mature amino acid sequence of AA707 α—is shown, below, as SEQ ID NO: 2:

```
HHNGTNGTMM QYFEWYLPND GNHWNRLNSD ASNLKSKGIT

AVWIPPAWKG ASQNDVGYGA YDLYDLGEFN QKGTVRTKYG

TRSQLQAAVT SLKNNGIQVY GDVVMNHKGG ADATEMVRAV

EVNPNNRNQE VTGEYTIEAW TRFDFPGRGN THSSFKWRWY

HFDGVDWDQS RRLNNRIYKF RGHGKAWDWE VDTENGNYDY

LMYADIDMDH PEVVNELRNW GVWYTNTLGL DGFRIDAVKH

IKYSFTRDWI NHVRSATGKN MFAVAEFWKN DLGAIENYLQ

KTNWNHSVFD VPLHYNLYNA SKSGGNYDMR NIFNGTVVQR

HPSHAVTFVD NHDSQPEEAL ESFVEEWFKP LAYALTLTRE

QGYPSVFYGD YYGIPTHGVP AMRSKIDPIL EARQKYAYGK

QNDYLDHHNI IGWTREGNTA HPNSGLATIM SDGAGGSKWM

FVGRNKAGQV WSDITGNRTG TVTINADGWG NFSVNGGSVS

IWVNK
```

Another closely related maltopentaose/maltohexaose-forming α-amylase is from a *Bacillus* sp. referred to as AA560. The mature amino acid sequence of AA560 is shown, below, as SEQ ID NO: 3:

```
HHNGTNGTMM QYFEWYLPND GNHWNRLRSD ASNLKDKGIS

AVWIPPAWKG ASQNDVGYGA YDLYDLGEFN QKGTIRTKYG

TRNQLQAAVN ALKSNGIQVY GDVVMNHKGG ADATEMVRAV

EVNPNNRNQE VSGEYTIEAW TKFDFPGRGN THSNFKWRWY

HFDGVDWDQS RKLNNRIYKF RGDGKGWDWE VDTENGNYDY

LMYADIDMDH PEVVNELRNW GVWYTNTLGL DGFRIDAVKH

IKYSFTRDWI NHVRSATGKN MFAVAEFWKN DLGAIENYLN

KTNWNHSVFD VPLHYNLYNA SKSGGNYDMR QIFNGTVVQR

HPMHAVTFVD NHDSQPEEAL ESFVEEWFKP LAYALTLTRE

QGYPSVFYGD YYGIPTHGVP AMKSKIDPIL EARQKYAYGR

QNDYLDHHNI IGWTREGNTA HPNSGLATIM SDGAGGNKWM

FVGRNKAGQV WTDITGNRAG TVTINADGWG NFSVNGGSVS

IWVNK
```

Based on amino acid sequence identity, another postulated maltopentaose/maltohexaose-forming α-amylase is from another *Bacillus* sp., and is herein referred to as AAI10. The mature amino acid sequence of AAI10 α-amylase is shown, below, as SEQ ID NO: 4:

```
HHDGTNGTIM QYFEWNVPND GQHWNRLHNN AQNLKNAGIT

AIWIPPAWKG TSQNDVGYGA YDLYDLGEFN QKGTVRTKYG

TKAELERAIR SLKANGIQVY GDVVMNHKGG ADFTERVQAV

EVNPQNRNQE VSGTYQIEAW TGFNFPGRGN QHSSFKWRWY

HFDGTDWDQS RQLANRIYKF RGDGKAWDWE VDTENGNYDY

LMYADVDMDH PEVINELNRW GVWYANTLNL DGFRLDAVKH

IKFSFMRDWL GHVRGQTGKN LFAVAEYWKN DLGALENYLS

KTNWTMSAFD VPLHYNLYQA SNSSGNYDMR NLLNGTLVQR

HPSHAVTFVD NHDTQPGEAL ESFVQGWFKP LAYATILTRE

QGYPQVFYGD YYGIPSDGVP SYRQQIDPLL KARQQYAYGR

QHDYFDHWDV IGWTREGNAS HPNSGLATIM SDGPGGSKWM

YVGRQKAGEV WHDMTGNRSG TVTINQDGWG HFFVNGGSVS

VWVKR
```

Amino acid sequence identity is summarized in Table 1. AA707, AA560 and AAI10 all have greater than 80% amino acid to AA2560.

TABLE 1

| Amino acid sequence identity of a-amylase | | | | |
|---|---|---|---|---|
| | AA2560 | AA707 | AA560 | AAI10 |
| AA2560 | — | 90.3 | 89.5 | 81.7 |
| AA707 | 90.3 | — | 95.5 | 79.8 |
| AA560 | 89.5 | 95.5 | — | 78.6 |
| AAI10 | 81.7 | 79.8 | 78.6 | — |

One feature of the variants of the invention is mutation at position 91 and/or at least one mutation at the bottom of the α-amylase TIM barrel structure. The barrel bottom residues have solvent accessible surface area greater than zero and lie in or adjacent to the core β-barrel structure, at the side of the barrel opposite of the active site, and at the side containing the N-terminal ends of each strand. Solvent accessible surface area was calculated using MOE 2018.01 (Chemical Computing Group, Montreal), using default parameters, and based on a homology model of AA2560 constructed with MOE 2018.01 using default parameters and the 1BLI structure from the pdb. Relevant residues are at positions 6, 7, 40, 96, 98, 100, 229, 230, 231, 262, 263, 285, 286, 287, 288, 322, 323, 324, 325, 362, 363 and 364, referring to SEQ ID NO: 1 for numbering. The residues lines of the base of the TIM barrel structure represents a primary architectural feature of α-amylases and many other enzymes. An exemplary mutation at residue 91 is substitution from a polar residue to a charged residue, particularly a positively-charged residue, such as arginine (i.e., X91R), which in the case of AA2560 is the specific substitution S91R.

Exemplary mutations in the barrel bottom residues are substitutions, including but not limited to X40N, X40D X100F, X100L, X263Y, X288D, X288K, X288Q, X324R, X324N, X324M, X364L and X364M, where "X" is the previously-existing amino acid residue in the wild-type parental α-amylase. Specific mutations with reference to AA2560 are T40N, T40D Y100F, Y100L, F263Y, S288D, S288K, S288Q, I324R, I324N, I324M, Y364L and Y364M.

Differently described, the variants have one, two three or more features including N or D at position 40, F or L at position 100, Y at position 263, D, K or Q at position 288, R, N or M at position 324 and L or M at position 364.

While the mutation at position 91 and the mutation at the barrel bottom result in superior performance advantages in combination, each mutation alone appears to produce a benefit, and some of the present variants have a mutation at only one position/structure.

The variants may additionally feature mutations in the loop that includes surface-exposed residues 167, 169, 171, 172 and 176, referring to SEQ ID NO: 1 for numbering. Exemplary mutations include but are not limited to the substitutions, X167F, X169H, X171Y, X172R, X172N and X176S and specifically, W167F, Q169H, R171Y, Q172R, Q172N and R176S. Differently described, the variants a feature substitutions including F at position 167, H at position 169, Y at position 171, R or N at position 172 and/or S at position 176, referring to SEQ ID NO: 1 for numbering.

The variants may additionally feature mutations at positions 116 and 281, which are believed to affect solubility. Exemplary mutations at these positions are the substitutions X116R and X281S, specifically the substitutions W116R and H281S.

The variants may additionally feature stabilizing mutations at positions 190 and/or 244, referring to SEQ ID NO: 1 for numbering. Such mutations have been well categorized, and are included in current, commercially-available α-amylases used for both cleaning, grain processing and textiles processing. Exemplary mutations in these residues are the substitutions X190P and X244A, E or Q, specifically E190P, S244A, S244E and S244Q. Mutations at positions 275 and 279 are also of interest in combination with mutations at position 190.

The variants may additionally feature mutations at positions 1, 7, 118, 195, 202, 206, 321, 245 and 459, referring to SEQ ID NO: 1 for numbering, which are included in current, commercially-available α-amylases or proposed for such applications.

The variants may further include a deletion in the $X_1G/S_1X_2G_2$ motif adjacent to the calcium-binding loop corresponding to R181, G182, T183, and G184, using SEQ ID NO: 1 for numbering. In some embodiments, the variant α-amylases include adjacent, pair-wise deletions of amino acid residues corresponding to R181 and G182, or T183 and G184. A deletion in amino acid residues corresponding to R181 and G182 may be referred to as "ΔRG," while a deletion in amino acid residues corresponding to the residue at position 183 (usually T, D, or H) and G184 may be referred to as "ΔTG," "ΔDG," "ΔHG" etc., as appropriate. Both pair-wise deletions appear to produce the same effect in α-amylases.

The variants may further include previously described mutations for use in other α-amylases having a similar fold and/or having 60% or greater amino acid sequence identity to (i) any of the well-known Bacillus α-amylases, e.g., from B. lichenifomis (i.e., BLA and LAT), B. stearothermophilus (i.e., BSG), and B. amyloliquifaciens (i.e., P00692, BACAM, and BAA), or hybrids, thereof, (ii) any α-amylases catagorized as Carbohydrate-Active Enzymes database (CAZy) Family 13 α-amylases or (iii) any amylase that has heretofore been referred to by the descriptive term, "Termamyl-like." Exemplary α-amylases include but are not limited to those from Bacillus sp. SG-1, Bacillus sp. 707, and α-amylases referred to as A7-7, SP722, DSM90 14 and KSM AP1378. Similarly, any of the combination of mutations described, herein, may produce performance advantages in these α-amylases, regardless of whether they have been described as maltopentaose/maltohexaose-producing α-amylases.

Specifically contemplated combinatorial variants are listed, below, using SEQ ID NO: 1 for numbering. As discussed, above, similar variants with ΔR183-ΔT184 instead of ΔR181-ΔG182 are expected to perform as well as those described in detail.

T40-S91-Q169-ΔR181-ΔG182-T183-H281
Q172-ΔR181-ΔG182-E190-S288
Q172-ΔR181-ΔG182-S244-S288-S474
S91-Q172-ΔR181-ΔG182-E190-I324
T40-S91-ΔR181-ΔG182-E190-F263
T40-S91-ΔR181-ΔG182-S244-Y364
S91-Q172-ΔR181-ΔG182-E190-I324
S91-W116-Q172-ΔR181-ΔG182-S244-H281-S288
T40-S91-Y100-W116-Q172-ΔR181-ΔG182-S244-H281
T40-S91-Q172-ΔR181-ΔG182-S244-F263-H281
S91-Q172-ΔR181-ΔG182-E190-I324
T40-S91-Q172-ΔR181-ΔG182-E190-H281-I324
Y364-ΔR181-ΔG182

In related α-amylases, including previous engineered α-amylases, the mutations may be described as:

X40-X91-X169-ΔR181-ΔG182-X183-X281
X172-ΔR181-ΔG182-X190-X288
X172-ΔR181-ΔG182-X244-X288-X474
X91-X172-ΔR181-ΔG182-X190-X324
X40-X91-ΔR181-ΔG182-X190-X263
X40-X91-ΔR181-ΔG182-X244-X364
X91-X172-ΔR181-ΔG182-X190-X324
X91-X116-X172-ΔR181-ΔG182-X244-X281-X288
X40-X91-X100-X116-X172-ΔR181-ΔG182-X244-X281
X40-X91-X172-ΔR181-ΔG182-X244-X263-X281
X91-X172-ΔR181-ΔG182-X190-X324
X40-X91-X172-ΔR181-ΔG182-X190-X281-X324
X364L-ΔR181-ΔG182

Such variants include those having two, three, four, five, six or more, of the following features: (a) D or N at position 40 and/or R at position 91, and (b) F at position 100, Y at position 263, D at position 288, M, N or R at position 324 and/or L at position 364, optionally in combination with (c) H at position 169, M at position 183M, N or S at position 281, N or Rat position 172, P at position 190, E, Q or R at position 244, R at position 474, R at position 116, optionally in combination with pairwise deletions at positions 181 and 182 or 183 and 184.

The specific substitutions in the tested variants are listed below:

T40N-S91R-Q169H-ΔR181-ΔG182-T183M-H281N
Q172R-ΔR181-ΔG182-E190P-S288D
Q172R-ΔR181-ΔG182-S244E-S288D-S474R
S91R-Q172R-ΔR181-ΔG182-E190P-I324M
T40N-S91R-ΔR181-ΔG182-E190P-F263Y
T40N-S91R-ΔR181-ΔG182-S244E-Y364L
S91R-Q172R-ΔR181-ΔG182-E190P-I324R
S91R-W116R-Q172R-ΔR181-ΔG182-S244E-H281S-S288D
T40N-S91R-Y100E-W116R-Q172N-ΔR181-ΔG182-S244Q-H281S
T40N-S91R-Q172R-ΔR181-ΔG182-S244Q-F263Y-H281S
S91R-Q172R-ΔR181-ΔG182-E190P-I324N
T40D-S91R-Q172R-ΔR181-ΔG182-E190P-H281S-I324R
Y364L-ΔR181-ΔG182

It will be appreciated that where an α-amylase naturally has a mutation listed above (i.e., where the wild-type α-amylase already comprised a residue identified as a mutation), then that particular mutation does not apply to that molecule. However, other described mutations may work in combination with the naturally-occurring residue at that position.

The present variant α-amylases may also include the substitution, deletion or addition of one or several amino acids in the amino acid sequence, for example less than 10, less than 9, less than 8, less than 7, less than 6, less than 5, less than 4, less than 3, or even less than 2 substitutions, deletions or additions. Such variants are expected to have similar activity to the α-amylases from which they were derived. The present variant α-amylases may also include minor deletions and/or extensions of one or a few residues at their N or C-termini. Such minor changes are unlikely to defeat the inventive concepts described, herein.

The present amylase may be "precursor," "immature," or "full-length," in which case they include a signal sequence, or "mature," in which case they lack a signal sequence. Mature forms of the polypeptides are generally the most useful. Unless otherwise noted, the amino acid residue numbering used herein refers to the mature forms of the respective amylase polypeptides.

In some embodiments, the variant α-amylase has at least 60%, at least 70%, at least 75%, at least 80%, at least 85%, at least 90%, at least 91%, at least 92%, at least 93%, at least 94%, at least 95%, at least 96%, at least 97%, at least 98%, or even at least 99%, but less than 100%, amino acid sequence identity to SEQ ID NO: 1, 2, 3 or 4, preferably to SEQ ID NO: 1

Preferred levels of the amylase in the composition of the invention include from about 0.01 to about 10 mg, more preferably from about 0.02 to about 5 mg, even more preferably from about 0.03 to about 2 mg of active amylase per gram of the composition.

Automatic Dishwashing Cleaning Composition

The automatic dishwashing cleaning composition can be in any physical form. It can be a loose powder, a gel or presented in unit dose form. Preferably it is in unit dose form, unit dose forms include pressed tablets and water-soluble packs. The automatic dishwashing cleaning composition of the invention is preferably presented in unit-dose form and it can be in any physical form including solid, liquid and gel form. The composition of the invention is very well suited to be presented in the form of a multi-compartment pack, more in particular a multi-compartment pack comprising compartments with compositions in different physical forms, for example a compartment comprising a composition in solid form and another compartment comprising a composition in liquid form. The composition is preferably enveloped by a water-soluble film such as polyvinyl alcohol. Especially preferred are compositions in unit dose form wrapped in a polyvinyl alcohol film having a thickness of less than 100 μm, preferably from 20 to 90 μm. The detergent composition of the invention weighs from about 8 to about 25 grams, preferably from about 10 to about 20 grams. This weight range fits comfortably in a dishwasher dispenser. Even though this range amounts to a low amount of detergent, the detergent has been formulated in a way that provides all the benefits mentioned herein above.

The composition is preferably phosphate free. By "phosphate-free" is herein understood that the composition comprises less than 1%, preferably less than 0.1% by weight of the composition of phosphate.

Complexing Agent System

For the purpose of this invention, a "complexing agent" is a compound capable of binding polyvalent ions such as calcium, magnesium, lead, copper, zinc, cadmium, mercury, manganese, iron, aluminium and other cationic polyvalent ions to form a water-soluble complex. The complexing agent has a logarithmic stability constant ([log K]) for Ca2+ of at least 3. The stability constant, log K, is measured in a solution of ionic strength of 0.1, at a temperature of 25° C.

The composition of the invention preferably comprises from 10% to 50% by weight of the composition of a complexing agent system. The complexing agent system comprises one or more complexing agents selected from the group consisting of methyl glycine diacetic acid (MGDA), citric acid, glutamic-N,N-diacetic acid (GLDA), iminodisuccinic acid (IDS), carboxy methyl inulin, L-Aspartic acid N,N-diacetic acid tetrasodium salt (ASDA) and mixtures thereof. Preferably, the complexing agent system comprises at least 10% by weight of the composition of MGDA. The complexing system may additionally comprise a complexing agent selected from the group consisting of citric acid, (GLDA), (IDS), carboxy methyl inulin, L-Aspartic acid N,N-diacetic acid tetrasodium salt (ASDA) and mixtures thereof. Preferably the complexing agent system comprises at least 10% by weight of the composition of MGDA and at least 10% by weight of the composition of citric acid. For the purpose of this invention, the term "acid", when referring to complexing agents, includes the acid and salts thereof.

In a preferred embodiment, the composition comprises at least 15%, more preferably from 20% to 40% by weight of the composition of MGDA, more preferably the tri-sodium salt of MGDA. Compositions comprising this high level of MGDA perform well in hard water and also in long and/or hot cycles.

The complexing agent system of the invention can further comprise citric acid.

Dispersant Polymer

A dispersant polymer can be used in any suitable amount from about 0.1 to about 20%, preferably from 0.2 to about 15%, more preferably from 0.3 to % by weight of the composition.

The dispersant polymer is capable to suspend calcium or calcium carbonate in an automatic dishwashing process.

The dispersant polymer has a calcium binding capacity within the range between 30 to 250 mg of Ca/g of dispersant polymer, preferably between 35 to 200 mg of Ca/g of dispersant polymer, more preferably 40 to 150 mg of Ca/g of dispersant polymer at 25° C. In order to determine if a polymer is a dispersant polymer within the meaning of the invention, the following calcium binding-capacity determination is conducted in accordance with the following instructions:

Calcium Binding Capacity Test Method

The calcium binding capacity referred to herein is determined via titration using a pH/ion meter, such as the Mettler Toledo SevenMulti™ bench top meter and a PerfectION™ comb Ca combination electrode. To measure the binding capacity a heating and stirring device suitable for beakers or tergotometer pots is set to 25° C., and the ion electrode with meter are calibrated according to the manufacturer's instructions. The standard concentrations for the electrode calibration should bracket the test concentration and should be measured at 25° C. A stock solution of 1000 mg/g of Ca is prepared by adding 3.67 g of $CaCl_2 \cdot 2H_2O$ into 1 L of deionised water, then dilutions are carried out to prepare three working solutions of 100 mL each, respectively comprising 100 mg/g, 10 mg/g, and 1 mg/g concentrations of Calcium. The 100 mg Ca/g working solution is used as the initial concentration during the titration, which is conducted at 25° C. The ionic strength of each working solution is adjusted by adding 2.5 g/L of NaCl to each. The 100 mL of 100 mg Ca/g working solution is heated and stirred until it reaches 25° C. The initial reading of Calcium ion concentration is conducted at when the solution reaches 25° C. using the ion electrode. Then the test polymer is added incrementally to the calcium working solution (at 0.01 g/L intervals) and measured after 5 minutes of agitation following each incremental addition. The titration is stopped when the solution reaches 1 mg/g of Calcium. The titration procedure is repeated using the remaining two calcium concentration working solutions. The binding capacity of the test polymer is calculated as the linear slope of the calcium concentrations measured against the grams/L of test polymer that was added.

The dispersant polymer preferably bears a negative net charge when dissolved in an aqueous solution with a pH greater than 6.

The dispersant polymer can bear also sulfonated carboxylic esters or amides, in order to increase the negative charge at lower pH and improve their dispersing properties in hard water. The preferred dispersant polymers are sulfonated/carboxylated polymers, i.e., polymer comprising both sulfonated and carboxylated monomers.

Preferably, the dispersant polymers are sulfonated derivatives of polycarboxylic acids and may comprise two, three, four or more different monomer units. The preferred copolymers contain:

At least one structural unit derived from a carboxylic acid monomer having the general formula (III):

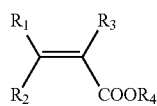

(III)

wherein $R_1$ to $R_3$ are independently selected from hydrogen, methyl, linear or branched saturated alkyl groups having from 2 to 12 carbon atoms, linear or branched mono or polyunsaturated alkenyl groups having from 2 to 12 carbon atoms, alkyl or alkenyl groups as aforementioned substituted with —NH2 or —OH, or —COOH, or $COOR_4$, where $R_4$ is selected from hydrogen, alkali metal, or a linear or branched, saturated or unsaturated alkyl or alkenyl group with 2 to 12 carbons;

Preferred carboxylic acid monomers include one or more of the following: acrylic acid, maleic acid, maleic anhydride, itaconic acid, citraconic acid, 2-phenylacrylic acid, cinnamic acid, crotonic acid, fumaric acid, methacrylic acid, 2-ethylacrylic acid, methylenemalonic acid, or sorbic acid. Acrylic and methacrylic acids being more preferred.

Optionally, one or more structural units derived from at least one non-ionic monomer having the general formula (IV):

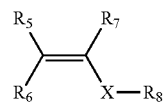

(IV)

Wherein $R_5$ to $R_7$ are independently selected from hydrogen, methyl, phenyl or hydroxyalkyl groups containing 1 to 6 carbon atoms, and can be part of a cyclic structure, X is an optionally present spacer group which is selected from —$CH_2$—, —COO—, —CONH— or —$CONR_8$—, and $R_8$ is selected from linear or branched, saturated alkyl radicals having 1 to 22 carbon atoms or unsaturated, preferably aromatic, radicals having from 6 to 22 carbon atoms.

Preferred non-ionic monomers include one or more of the following: butene, isobutene, pentene, 2-methylpent-1-ene, 3-methylpent-1-ene, 2,4,4-trimethylpent-1-ene, 2,4,4-trimethylpent-2-ene, cyclopentene, methylcyclopentene, 2-methyl-3-methyl-cyclopentene, hexene, 2,3-dimethylhex-1-ene, 2,4-dimethylhex-1-ene, 2,5-dimethylhex-1-ene, 3,5-dimethylhex-1-ene, 4,4-dimethylhex-1-ene, cyclohexene, methylcyclohexene, cycloheptene, alpha olefins having 10 or more carbon atoms such as, dec-1-ene, dodec-1-ene, hexadec-1-ene, octadec-1-ene and docos-1-ene, preferred aromatic monomers are styrene, alpha methylstyrene, 3-methylstyrene, 4-dodecylstyrene, 2-ethyl-4-bezylstyrene, 4-cyclohexylstyrene, 4-propylstyrol, 1-vinylnaphtalene, 2-vinylnaphtalene; preferred carboxylic ester monomers are methyl (meth)acrylate, ethyl (meth)acrylate, propyl (meth)acrylate, t-butyl (meth)acrylate, pentyl (meth)acrylate, hexyl (meth)acrylate, 2-ethylhexyl (meth)acrylate, octyl (meth)acrylate, lauryl (meth)acrylate, stearyl (meth)acrylate and behenyl (meth)acrylate; preferred amides are N-methyl acrylamide, N-ethyl acrylamide, N-t-butyl acrylamide, N-2-ethylhexyl acrylamide, N-octyl acrylamide, N-lauryl acrylamide, N-stearyl acrylamide, N-behenyl acrylamide.

And at least one structural unit derived from at least one sulfonic acid monomer having the general formula (V) and (VI):

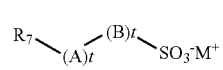

(V)

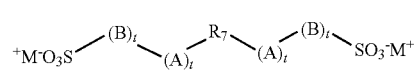

(VI)

wherein $R_7$ is a group comprising at least one sp2 bond, A is O, N, P, S, an amido or ester linkage, B is a mono- or polycyclic aromatic group or an aliphatic group, each t is independently 0 or 1, and M+ is a cation. In one aspect, $R_7$ is a C2 to C6 alkene. In another aspect, R7 is ethene, butene or propene.

Preferred sulfonated monomers include one or more of the following: 1-acrylamido-1-propanesulfonic acid, 2-acrylamido-2-propanesulfonic acid, 2-acrylamido-2-methyl-1-propanesulfonic acid, 2-methacrylamido-2-methyl-1-propanesulfonic acid, 3-methacrylamido-2-hydroxypropanesulfonic acid, allylsulfonic acid, methallylsulfonic acid, allyloxybenzenesulfonic acid, methallyloxybenzenesulfonic acid, 2-hydroxy-3-(2-propenyloxy) propanesulfonic acid, 2-methyl-2-propen-1-sulfonic acid, styrenesulfonic acid, vinylsulfonic acid, 3-sulfopropyl, 3-sulfo-propylmethacrylate, sulfomethacrylamide, sulfomethylmethacrylamide and mixtures of said acids or their water-soluble salts.

Preferably, the polymer comprises the following levels of monomers: from about 40 to about 90%, preferably from about 60 to about 90% by weight of the polymer of one or more carboxylic acid monomer; from about 5 to about 50%, preferably from about 10 to about 40% by weight of the polymer of one or more sulfonic acid monomer; and optionally from about 1% to about 30%, preferably from about 2 to about 20% by weight of the polymer of one or more non-ionic monomer. An especially preferred polymer comprises about 70% to about 80% by weight of the polymer of at least one carboxylic acid monomer and from about 20% to about 30% by weight of the polymer of at least one sulfonic acid monomer.

In the polymers, all or some of the carboxylic or sulfonic acid groups can be present in neutralized form, i.e. the acidic hydrogen atom of the carboxylic and/or sulfonic acid group in some or all acid groups can be replaced with metal ions, preferably alkali metal ions and in particular with sodium ions.

The carboxylic acid is preferably (meth)acrylic acid. The sulfonic acid monomer is preferably 2-acrylamido-2-propanesulfonic acid (AMPS).

Preferred commercially available polymers include: Alcosperse 240, Aquatreat AR 540 and Aquatreat MPS supplied by Alco Chemical; Acumer 3100, Acumer 2000, Acusol 587G and Acusol 588G supplied by Rohm & Haas; Goodrich K-798, K-775 and K-797 supplied by BF Goodrich; and ACP 1042 supplied by ISP technologies Inc. Particularly preferred polymers are Acusol 587G and Acusol 588G supplied by Rohm & Haas.

Suitable dispersant polymers include anionic carboxylic polymer of low molecular weight. They can be homopolymers or copolymers with a weight average molecular weight of less than or equal to about 200,000 g/mol, or less than or equal to about 75,000 g/mol, or less than or equal to about 50,000 g/mol, or from about 3,000 to about 50,000 g/mol, preferably from about 5,000 to about 45,000 g/mol. The dispersant polymer may be a low molecular weight homopolymer of polyacrylate, with an average molecular weight of from 1,000 to 20,000, particularly from 2,000 to 10,000, and particularly preferably from 3,000 to 5,000.

The dispersant polymer may be a copolymer of acrylic with methacrylic acid, acrylic and/or methacrylic with maleic acid, and acrylic and/or methacrylic with fumaric acid, with a molecular weight of less than 70,000. Their molecular weight ranges from 2,000 to 80,000 and more preferably from 20,000 to 50,000 and in particular 30,000 to 40,000 g/mol. and a ratio of (meth)acrylate to maleate or fumarate segments of from 30:1 to 1:2.

The dispersant polymer may be a copolymer of acrylamide and acrylate having a molecular weight of from 3,000 to 100,000, alternatively from 4,000 to 20,000, and an acrylamide content of less than 50%, alternatively less than 20%, by weight of the dispersant polymer can also be used. Alternatively, such dispersant polymer may have a molecular weight of from 4,000 to 20,000 and an acrylamide content of from 0% to 15%, by weight of the polymer.

Dispersant polymers suitable herein also include itaconic acid homopolymers and copolymers.

Alternatively, the dispersant polymer can be selected from the group consisting of alkoxylated polyalkyleneimines, alkoxylated polycarboxylates, polyethylene glycols, styrene co-polymers, cellulose sulfate esters, carboxylated polysaccharides, amphiphilic graft copolymers and mixtures thereof.

Bleaching System

The composition of the invention preferably comprises a bleaching system comprising a high level of bleach, preferably percarbonate in combination with a bleach activator or a bleach catalyst or both. Preferably the bleach activator is TAED and the bleach catalyst is a manganese bleach catalyst.

Bleach

The composition of the invention preferably comprises from about 10 to about 20%, more preferably from about 12 to about 18% of bleach, preferably percarbonate, by weight of the composition.

Inorganic and organic bleaches are suitable for use herein. Inorganic bleaches include perhydrate salts such as perborate, percarbonate, perphosphate, persulfate and persilicate salts. The inorganic perhydrate salts are normally the alkali metal salts. The inorganic perhydrate salt may be included as the crystalline solid without additional protection. Alternatively, the salt can be coated. Suitable coatings include sodium sulphate, sodium carbonate, sodium silicate and mixtures thereof. Said coatings can be applied as a mixture applied to the surface or sequentially in layers.

Alkali metal percarbonates, particularly sodium percarbonate is the preferred bleach for use herein. The percarbonate is most preferably incorporated into the products in a coated form which provides in-product stability.

Potassium peroxymonopersulfate is another inorganic perhydrate salt of utility herein. Typical organic bleaches are organic peroxyacids, especially dodecanediperoxoic acid, tetradecanediperoxoic acid, and hexadecanediperoxoic acid. Mono- and diperazelaic acid, mono- and diperbrassylic acid are also suitable herein. Diacyl and Tetraacylperoxides, for instance dibenzoyl peroxide and dilauroyl peroxide, are other organic peroxides that can be used in the context of this invention.

Further typical organic bleaches include the peroxyacids, particular examples being the alkylperoxy acids and the arylperoxy acids. Preferred representatives are (a) peroxybenzoic acid and its ring-substituted derivatives, such as alkylperoxybenzoic acids, but also peroxy-α-naphthoic acid and magnesium monoperphthalate, (b) the aliphatic or substituted aliphatic peroxy acids, such as peroxylauric acid, peroxystearic acid, ε-phthalimidoperoxycaproic acid[phthaloiminoperoxyhexanoic acid (PAP)], o-carboxybenzamidoperoxycaproic acid, N-nonenylamidoperadipic acid and N-nonenylamidopersuccinates, and (c) aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyldi(6-aminopercaproic acid).

Bleach Activators

Bleach activators are typically organic peracid precursors that enhance the bleaching action in the course of cleaning at temperatures of 60° C. and below. Bleach activators suitable for use herein include compounds which, under perhydrolysis conditions, give aliphatic peroxoycarboxylic acids having preferably from 1 to 12 carbon atoms, in particular from 2 to 10 carbon atoms, and/or optionally substituted perbenzoic acid. Suitable substances bear O-acyl and/or N-acyl groups of the number of carbon atoms specified and/or optionally substituted benzoyl groups. Preference is given to polyacylated alkylenediamines, in particular tetraacetylethylenediamine (TAED), acylated triazine derivatives, in particular 1,5-diacetyl-2,4-dioxohexahydro-1,3,5-triazine (DADHT), acylated glycolurils, in particular tetraacetylglycoluril (TAGU), N-acylimides, in particular N-nonanoylsuccinimide (NOSI), acylated phenolsulfonates, in particular n-nonanoyl- or isononanoyloxybenzenesulfonate (n- or iso-NOBS), decanoyloxybenzoic acid (DOBA), carboxylic anhydrides, in particular phthalic anhydride, acylated polyhydric alcohols, in particular triacetin, ethylene glycol diacetate and 2,5-diacetoxy-2,5-dihydrofuran and also triethylacetyl citrate (TEAC). If present the composition of the invention comprises from 0.01 to 5, preferably from 0.2 to 2% by weight of the composition of bleach activator, preferably TAED.

Bleach Catalyst

The composition herein preferably contains a bleach catalyst, preferably a metal containing bleach catalyst. More preferably the metal containing bleach catalyst is a transition metal containing bleach catalyst, especially a manganese or cobalt-containing bleach catalyst. Bleach catalysts preferred for use herein include manganese triazacyclononane and related complexes; Co, Cu, Mn and Fe bispyridylamine and related complexes; and pentamine acetate cobalt(III) and related complexes. Especially preferred bleach catalyst for use herein are 1,4,7-trimethyl-1,4,7-triazacyclononane (Me-TACN) and 1,2,4,7-tetramethyl-1,4,7-triazacyclononane (Me/Me-TACN). Especially preferred composition for use herein comprises 1,4,7-trimethyl-1,4,7-triazacyclononane (Me-TACN) and/or 1,2,4,7-tetramethyl-1,4,7-triazacyclononane (Me/Me-TACN).

Preferably the composition of the invention comprises from 0.001 to 0.5, more preferably from 0.002 to 0.05%, more preferably from 0.005 to 0.075% of bleach catalyst by weight of the composition. Preferably the bleach catalyst is a manganese bleach catalyst.

Inorganic Builder

The composition of the invention preferably comprises an inorganic builder. Suitable inorganic builders are selected from the group consisting of carbonate, silicate and mixtures thereof. Especially preferred for use herein is sodium carbonate. Preferably the composition of the invention comprises from 5 to 60%, more preferably from 10 to 50% and especially from 15 to 45% of sodium carbonate by weight of the composition.

Surfactant

Surfactants suitable for use herein include non-ionic surfactants, preferably the compositions are free of any other surfactants. Traditionally, non-ionic surfactants have been used in automatic dishwashing for surface modification purposes in particular for sheeting to avoid filming and spotting and to improve shine. It has been found that non-ionic surfactants can also contribute to prevent redeposition of soils.

Preferably the composition of the invention comprises a non-ionic surfactant or a non-ionic surfactant system, more preferably the non-ionic surfactant or a non-ionic surfactant system has a phase inversion temperature, as measured at a concentration of 1% in distilled water, between 40 and 70° C., preferably between 45 and 65° C. By a "non-ionic surfactant system" is meant herein a mixture of two or more non-ionic surfactants. Preferred for use herein are non-ionic surfactant systems. They seem to have improved cleaning and finishing properties and better stability in product than single non-ionic surfactants.

Phase inversion temperature is the temperature below which a surfactant, or a mixture thereof, partitions preferentially into the water phase as oil-swollen micelles and above which it partitions preferentially into the oil phase as water swollen inverted micelles. Phase inversion temperature can be determined visually by identifying at which temperature cloudiness occurs.

The phase inversion temperature of a non-ionic surfactant or system can be determined as follows: a solution containing 1% of the corresponding surfactant or mixture by weight of the solution in distilled water is prepared. The solution is stirred gently before phase inversion temperature analysis to ensure that the process occurs in chemical equilibrium. The phase inversion temperature is taken in a thermostable bath by immersing the solutions in 75 mm sealed glass test tube. To ensure the absence of leakage, the test tube is weighed before and after phase inversion temperature measurement. The temperature is gradually increased at a rate of less than 1° C. per minute, until the temperature reaches a few degrees below the pre-estimated phase inversion temperature. Phase inversion temperature is determined visually at the first sign of turbidity.

Suitable nonionic surfactants include: i) ethoxylated non-ionic surfactants prepared by the reaction of a monohydroxy alkanol or alkyphenol with 6 to 20 carbon atoms with preferably at least 12 moles particularly preferred at least 16 moles, and still more preferred at least 20 moles of ethylene oxide per mole of alcohol or alkylphenol; ii) alcohol alkoxylated surfactants having a from 6 to 20 carbon atoms and at least one ethoxy and propoxy group. Preferred for use herein are mixtures of surfactants i) and ii).

Other suitable non-ionic surfactants are epoxy-capped poly(oxyalkylated) alcohols represented by the formula:

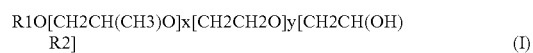

(I)

wherein R1 is a linear or branched, aliphatic hydrocarbon radical having from 4 to 18 carbon atoms; R2 is a linear or branched aliphatic hydrocarbon radical having from 2 to 26 carbon atoms; x is an integer having an average value of from 0.5 to 1.5, more preferably about 1; and y is an integer having a value of at least 15, more preferably at least 20.

Preferably, the surfactant of formula I, at least about 10 carbon atoms in the terminal epoxide unit [CH2CH(OH)R2]. Suitable surfactants of formula I, according to the present invention, are Olin Corporation's POLY-TERGENT® SLF-18B nonionic surfactants, as described, for example, in WO 94/22800, published Oct. 13, 1994 by Olin Corporation.

Enzymes

Proteases

The composition of the invention can comprise one or more proteases. A mixture of two or more proteases can contribute to an enhanced cleaning across a broader temperature, cycle duration, and/or substrate range, and provide superior shine benefits, especially when used in conjunction with an anti-redeposition agent and/or a sulfonated polymer.

Suitable proteases for use herein include metalloproteases and serine proteases, including neutral or alkaline microbial serine proteases, such as subtilisins (EC 3.4.21.62). Suitable proteases include those of animal, vegetable or microbial origin. In one aspect, such suitable protease may be of microbial origin. The suitable proteases include chemically or genetically modified mutants of the aforementioned suitable proteases. In one aspect, the suitable protease may be a serine protease, such as an alkaline microbial protease or/and a trypsin-type protease. Examples of suitable neutral or alkaline proteases include:

(a) subtilisins (EC 3.4.21.62), especially those derived from Bacillus, such as Bacillus sp., B. lentus, B. alkalophilus, B. subtilis, B. amyloliquefaciens, B. pumilus, B. gibsonii, and B. akibaii described in WO2004067737, WO2015091989, WO2015091990, WO2015024739, WO2015143360, U.S. Pat. Nos. 6,312,936 B1, 5,679,630, 4,760,025, DE102006022216A1, DE102006022224A1, WO2015089447, WO2015089441, WO2016066756, WO2016066757, WO2016069557, WO2016069563, WO2016069569.

(b) trypsin-type or chymotrypsin-type proteases, such as trypsin (e.g., of porcine or bovine origin), including the Fusarium protease described in WO 89/06270 and the chymotrypsin proteases derived from Cellumonas described in WO 05/052161 and WO 05/052146.

(c) metalloproteases, especially those derived from Bacillus amyloliquefaciens decribed in WO07/044993A2; from Bacillus, Brevibacillus, Thermoactinomyces, Geobacillus, Paenibacillus, Lysinibacillus or Streptomyces spp. Described in WO2014194032, WO2014194054 and WO2014194117; from Kribella alluminosa described in WO2015193488; and from Streptomyces and Lysobacter described in WO2016075078.

(d) protease having at least 90% identity to the subtilase from Bacillus sp. TY145, NCIMB 40339, described in WO92/17577 (Novozymes A/S), including the variants of this Bacillus sp TY145 subtilase described in WO2015024739, and WO2016066757.

Especially preferred additional proteases for the composition of the invention are proteasesdemonstrating at least 90%, preferably at least 95%, more preferably at least 98%, even more preferably at least 99% and especially 100% identity with SEQ ID NO:6, comprising substitutions in one or more, or two or more or three or more of the following positions versus SEQ ID NO:6:

S3V, S9R, A13V, A15T, G20*, L21F, I35V, N60D, V66A, N74D, S85N/R, S97SE, S97AD, S97D/G, S99G/M/D/E, S101A, V102E/I, G116V/R, S126F/L, P127Q, S128A, S154D, G157S, Y161A, R164S, A188P, V199I, Q200C/E/I/K/T/V/W/L, Y203W, N212D, M216S/F, A222V, Q239R/F, T249R, N255D and L256E/N/Q/D Preferred proteases include those with at least 90%, preferably at least 95% identity to SEQ ID NO:6 comprising the following mutations:
S9R+A13V+A15T+I35V+N60D+Q239F; or
S9R+A15T+G20*+L21F+N60D+Q239N; or
S9R+A15T+V66A+S97G+A222V+Q239R+N255D; or
S9R+A15T+V66A+N74D+Q239R; or
S9R+A15T+V66A+N212D+Q239R; or
S99SE; or
S99AD; or
N74D+S85R+G116R+S126L+P127Q+S128A; or
N74D+S85R+G116R+S126L+P127Q+S128A+S182D+V238R; or
G116V+S126L+P127Q+S128A; or
S99M+G116V+S126L+P127Q+S128A.

Another set of especially preferred proteases are those demonstrating at least 90%, preferably at least 95%, more preferably at least 98%, identity with SEQ ID NO:5, comprising substitutions in one or more, or two or more or three or more of the following positions versus SEQ ID NO:5:

S039E, I43V, A47V, P54T, T56Y, N074D, L80V, N085R, E087D, S099R, N114Q, M117I, S126A, D127E, F128G/D/E, G160Q, R179Q, N198G/A/K/L/Q/R/T/V/S/L, R207Q, M211Q/N/L, N212Q/S, N242D, N253P, and Q256E.

Preferred proteases include those with at least 90%, preferably at least 95% identity to SEQ ID NO:5 comprising one of the following sets of mutations:
S039E-N074D-S099R-S126A-D127E-F128G-M211L-N242D; or
S039E-N074D-S099R-S126A-D127E-F128G-Q256E; or
S039E-N074D-S099R-S126A-D127E-F128G-M211L; or
S039E-N074D-S099R-S126A-D127E-F128G-Q200L; or
S039E-N074D-S099R-S126A-D127E-F128G-Q200L-M211L; or
S039E-N074D-S099R-S126A-D127E-F128G-Q200L-Q256E; or
S039E-N074D-S099R-S126A-D127E-F128G-Q200L-N242D-Q256E; or
S039E-N074D-N085R-S099R-S126A-D127E-F128G-M211L-N212S; or
A37T-S39E-I43V-A47V-T56Y-I80V-N85S-E87D-S99R-T114Q-S126D-D127S-F128A-N242D; or
A37T-S39E-I43V-A47V-T56Y-I80V-N85S-E87D-T114Q-S126G-D127T-F128E-N242D; or
A37T-S39E-I43V-A47V-T56Y-I80V-N85S-E87D-S99R-T114Q-D127A-F128C-N242D; or
A37T-S39E-I43V-A47V-P54T-T56Y-I80V-N85S-E87D-S99E-T114Q-S126T-F128A-N242D; or
A37T-S39E-I43V-A47V-P54T-T56Y-I80V-N85S-E87D-S99R-T114Q-S126V-D127A-F128T-N242D; or
A37T-S39E-I43V-A47V-P54T-T56Y-I80V-N85S-E87D-S99R-T114Q-F128E-N242D; or
A37T-S39E-I43V-A47V-T56Y-I80V-N85S-E87D-S99E-T114Q-D127E-F128G-N242D; or
A37T-S39E-I43V-A47V-P54T-T56Y-I80V-N85S-E87D-S99R-T114Q-S126T-D127E-F128A-N242D; or
A37T-S39E-I43V-A47V-T56Y-I80V-N85S-E87D-T114Q-D127P-F128E-N242D; or
A37T-S39E-I43V-A47V-P54T-T56Y-I80V-N85S-E87D-S99R-T114Q-S126G-D127E-F128D-N242D; or
A37T-S39E-I43V-A47V-T56Y-I80V-N85S-E87D-S99R-T114Q-F128E-N242D; or
A37T-S39E-I43V-A47V-T56Y-I80V-N85S-E87D-S99R-T114Q-S126T-D127E-F128E-N242D; or
A37T-S39E-I43V-A47V-P54T-T56Y-I80V-N85S-E87D-S99R-T114Q-S126A-D127E-F128G-N242D; or
A37T-S39E-I43V-A47V-P54T-T56Y-I80V-N85S-E87D-S99R-T114Q-D127G-F128P-N242D; or
A37T-S39E-I43V-A47V-P54T-T56Y-I80V-N85S-E87D-S99R-T114Q-D127G-F128E-N242D; or
A37T-S39E-I43V-A47V-P54T-T56Y-I80V-N85S-E87D-S99R-T114Q-S126A-F128G-N242D; or
A37T-S39E-I43V-A47V-P54T-T56Y-I80V-N85S-E87D-S99R-T114Q-S126A-D127E-F128G-N242D; or
S039E-N074D-S099R-S126A-D127E-F128G-N198G-M211Q; or
S039E-N074D-S099R-S126A-D127E-F128G-N198G-M211Q-N212Q; or
S039E-N074D-S099R-S126A-D127E-F128G-N198A-M211Q-N212Q; or
S039E-N074D-S099R-N116R-S126A-D127E-F128G-M211Q-N242D-Q256E In one preferred aspect the composition of the invention may comprise more than one protease, preferably one protease with at least 95% identity to SEQ ID NO:6 and one protease with at least 95% identity to SEQ ID NO:5

Suitable commercially available additional protease enzymes include those sold under the trade names Alcalase®, Savinase®, Primase®, Durazym®, Polarzyme®, Kannase®, Liquanase®, Liquanase Ultra®, Savinase Ultra®, Savinase Evity®, Progress Uno®, Ovozyme®, Neutrase®, Everlase®, Coronase®, the Blaze® series (including Blaze®, Blaze Ultra®, Blaze Evity®, Blaze Pro®) and Esperase® by Novozymes A/S (Denmark); those sold under the tradename Maxatase®, Maxacal®, Maxapem®, Properase®, Purafect®, Purafect Prime®, Purafect Ox®, FN3®, FN4®, Excellase®, Ultimase®, Extremase® and Purafect OXP® by Dupont; those sold under the tradename Opticlean® and Optimase® by Solvay Enzymes; and those available from Henkel/Kemira, namely BLAP (sequence shown in FIG. 29 of U.S. Pat. No. 5,352,604 with the following mutations S99D+S101R+S103A+V104I+G159S, hereinafter referred to as BLAP), BLAP R (BLAP with S3T+V4I+V199M+V205I+L217D), BLAP X (BLAP with S3T+V4I+V205I) and BLAP F49 (BLAP with S3T+V4I+A194P+V199M+V205I+L217D); and KAP (*Bacillus alkalophilus* subtilisin with mutations A230V+S256G+S259N) from Kao.

Especially preferred for use herein in combination with the amylase of this invention is one or more of:

(a) commercial proteases selected from the group consisting of Blaze®, Ultimase®, Everlase®, Savinase®, Savinase Evity®, Savinase Ultra®, Excellase®, Extremase®, Ovozyme®, Coronase® Blaze Evity® and Blaze Pro®;

(b) the proteases with a to least 95% identity to SEQ ID NO:5 specified above.

Preferred levels of protease in the product of the invention include from about 0.05 to about 10, more preferably from about 0.5 to about 7 and especially from about 1 to about 6 mg of active protease/g of composition.

Additional Amylases

The composition of the invention may comprise an additional amylase. Suitable additional alpha-amylases include those of bacterial or fungal origin. Chemically or genetically modified mutants (variants) are included. A preferred alkaline alpha-amylase is derived from a strain of *Bacillus*, such as *Bacillus licheniformis, Bacillus amyloliquefaciens, Bacillus stearothermophilus, Bacillus subtilis*, or other *Bacillus* sp., such as *Bacillus* sp. NCBI 12289, NCBI 12512, NCBI 12513, DSM 9375 (U.S. Pat. No. 7,153,818) DSM 12368, DSMZ no. 12649, KSM AP1378 (WO 97/00324), KSM K36 or KSM K38 (EP 1,022,334). Preferred amylases include:

(a) variants described in WO 96/23873, WO00/60060, WO06/002643 and WO2017/192657, especially the variants with one or more substitutions in the following positions versus the AA560 enzyme listed as SEQ ID NO. 12 in WO06/002643:

26, 30, 33, 82, 37, 106, 118, 128, 133, 149, 150, 160, 178, 182, 186, 193, 202, 214, 231, 246, 256, 257, 258, 269, 270, 272, 283, 295, 296, 298, 299, 303, 304, 305, 311, 314, 315, 318, 319, 339, 345, 361, 378, 383, 419, 421, 437, 441, 444, 445, 446, 447, 450, 461, 471, 482, 484, preferably that also contain the deletions of D183* and G184*.

(b) variants exhibiting at least 90% identity with SEQ ID No. 4 in WO06/002643, the wild-type enzyme from *Bacillus* SP722, especially variants with deletions in the 183 and 184 positions and variants described in WO 00/60060, WO2011/100410 and WO2013/003659which are incorporated herein by reference.

(c) variants exhibiting at least 95% identity with the wild-type enzyme from *Bacillus* sp.707 (SEQ ID NO:7 in U.S. Pat. No. 6,093,562), especially those comprising one or more of the following mutations M202, M208, S255, R172, and/or M261. Preferably said amylase comprises one or more of M202L, M202V, M202S, M202T, M202I, M202Q, M202W, S255N and/or R172Q. Particularly preferred are those comprising the M202L or M202T mutations.

(d) variants described in WO 09/149130, preferably those exhibiting at least 90% identity with SEQ ID NO: 1 or SEQ ID NO:2 in WO 09/149130, the wild-type enzyme from Geobacillus Stearophermophilus or a truncated version thereof.

(e) variants exhibiting at least 89% identity with SEQ ID NO:1 in WO2016091688, especially those comprising deletions at positions H183+G184 and additionally one or more mutations at positions 405, 421, 422 and/or 428.

(f) variants exhibiting at least 60% amino acid sequence identity with the "PcuAmyl α-amylase" from Paenibacillus curdlanolyticus YK9 (SEQ ID NO:3 in WO2014099523).

(g) variants exhibiting at least 60% amino acid sequence identity with the "CspAmy2 amylase" from *Cytophaga* sp. (SEQ ID NO:1 in WO2014164777).

(h) variants exhibiting at least 85% identity with AmyE from *Bacillus subtilis* (SEQ ID NO:1 in WO2009149271).

(i) variants exhibiting at least 90% identity with the wild-type amylase from *Bacillus* sp. KSM-K38 with accession number AB051102.

(j) variants exhibiting at least 90%, preferably at least 95%, preferably at least 98% identity with the mature amino acid sequence of AAI10 from *Bacillus* sp (SEQ ID NO:7 in WO2016180748)

(k) variants exhibiting at least 80% identity with the mature amino acid sequence of *Alicyclobacillus* sp. amylase (SEQ ID NO:8 in WO2016180748)

Preferably the amylase is an engineered enzyme, wherein one or more of the amino acids prone to bleach oxidation have been substituted by an amino acid less prone to oxidation. In particular it is preferred that methionine residues are substituted with any other amino acid. In particular it is preferred that the methionine most prone to oxidation is substituted. Preferably the methionine in a position equivalent to 202 in the AA560 enzyme listed as SEQ ID NO. 12 in WO06/002643 is substituted. Preferably, the methionine at this position is substituted with threonine or leucine, preferably leucine.

Suitable commercially available alpha-amylases include DURAMYL®, LIQUEZYME®, TERMAMYL®, TERMAMYL ULTRA®, NATALASE®, SUPRAMYL®, STAINZYME®, STAINZYME PLUS®, FUNGAMYL®, AMPLIFY®, ATLANTIC®, INTENSA® and BAN® (Novozymes A/S, Bagsvaerd, Denmark), KEMZYM® AT 9000 Biozym Biotech Trading GmbH Wehlistrasse 27b A-1200 Wien Austria, RAPIDASE®, PURASTAR®, ENZYSIZE®, OPTISIZE HT PLUS®, POWERASE®, PREFERENZ S® series (including PREFERENZ S1000® and PREFERENZ S2000® and PURASTAR OXAM® (DuPont., Palo Alto, California) and KAM® (Kao, 14-10 Nihonbashi Kayabacho, 1-chome, Chuo-ku Tokyo 103-8210, Japan). In one aspect, suitable amylases include ATLANTIC®, STAINZYME®, POWERASE®, INTENSA®, AMPLIFY® and STAINZYME PLUS® and mixtures thereof.

Preferably, the composition of the invention comprises at least 0.01 mg, preferably from about 0.02 to about 10, more preferably from about 0.1 to about 6, especially from about 0.2 to about 5 mg of active amylase/g of composition.

The composition of the invention may comprise two or more amylases, where preferably the first amylase is a variant of SEQ ID NO:1 and the second amylase is a variant of SEQ ID NO:2, 3 or 4.

Preferably, the protease and/or amylase of the composition of the invention are in the form of granulates, the granulates comprise more than 29% of sodium sulfate by weight of the granulate and/or the sodium sulfate and the active enzyme (protease and/or amylase) are in a weight ratio of between 3:1 and 100:1 or preferably between 4:1 and 30:1 or more preferably between 5:1 and 20:1.

Crystal Growth Inhibitor

Crystal growth inhibitors are materials that can bind to calcium carbonate crystals and prevent further growth of species such as aragonite and calcite.

Examples of effective crystal growth inhibitors include phosphonates, polyphosphonates, inulin derivatives, polyitaconic acid homopolymers and cyclic polycarboxylates.

Suitable crystal growth inhibitors may be selected from the group comprising HEDP (1-hydroxyethylidene 1,1-diphosphonic acid), carboxymethylinulin (CMI), tricarballylic acid and cyclic carboxylates. For the purposes of this invention the term carboxylate covers both the anionic form and the protonated carboxylic acid form.

Cyclic carboxylates contain at least two, preferably three or preferably at least four carboxylate groups and the cyclic structure is based on either a mono- or bi-cyclic alkane or a heterocycle. Suitable cyclic structures include cyclopropane, cyclobutane, cyclohexane or cyclopentane or cycloheptane, bicyclo-heptane or bicyclo-octane and/or tetrhaydrofuran. One preferred crystal growth inhibitor is cyclopentane tetracarboxylate.

Cyclic carboxylates having at least 75%, preferably 100% of the carboxylate groups on the same side, or in the "cis" position of the 3D-structure of the cycle are preferred for use herein. It is preferred that the two carboxylate groups, which are on the same side of the cycle are in directly neighbouring or "ortho" positions.

Preferred crystal growth inhibitors include HEDP, tricarballylic acid, tetrahydrofurantetracarboxylic acid (THFTCA) and cyclopentanetetracarboxylic acid (CPTCA). The THFTCA is preferably in the 2c,3t,4t,5c-configuration, and the CPTCA in the cis,cis,cis,cis-configuration. Especially preferred crystal growth inhibitor for use herein is HEDP.

Also, preferred for use herein are partially decarboxylated polyitaconic acid homopolymers, preferably having a level of decarboxylation is in the range of 50 mole % to 90 mole %. Especially preferred polymer for use herein is Itaconix TSI® provided by Itaconix.

The crystal growth inhibitors are present preferably in a quantity from about 0.01 to about 10%, particularly from about 0.02 to about 5% and in particular, from 0.05 to 3% by weight of the composition.

Metal Care Agents

Metal care agents may prevent or reduce the tarnishing, corrosion or oxidation of metals, including aluminium, stainless steel and non-ferrous metals, such as silver and copper. Preferably the composition of the invention comprises from 0.1 to 5%, more preferably from 0.2 to 4% and especially from 0.3 to 3% by weight of the product of a metal care agent, preferably the metal care agent is benzo triazole (BTA).

Glass Care Agents

Glass care agents protect the appearance of glass items during the dishwashing process. Preferably the composition of the invention comprises from 0.1 to 5%, more preferably from 0.2 to 4% and specially from 0.3 to 3% by weight of the composition of a metal care agent, preferably the glass care agent is a zinc containing material, specially hydrozincite. Other suitable glass care agents are polyethyleneimine (PEI). A particularly preferred PEI is Lupasol® FG, supplied by BASF.

The automatic dishwashing composition of the invention preferably has a pH as measured in 1% weight/volume aqueous solution in distilled water at 20° C. of from about 9 to about 12, more preferably from about 10 to less than about 11.5 and especially from about 10.5 to about 11.5.

The automatic dishwashing composition of the invention preferably has a reserve alkalinity of from about 10 to about 20, more preferably from about 12 to about 18 at a pH of 9.5 as measured in NaOH with 100 grams of product at 20° C.

A preferred automatic dishwashing composition of the invention comprises:
i) from 10 to 20% by weight of the composition of bleach, preferably sodium percarbonate;
ii) TAED;
iii) optionally but preferably from 5 to 50% by weight of the composition of an inorganic builder, preferably sodium carbonate;
iv) optionally but preferably from 2 to 10% by weight of the composition of a non-ionic surfactant;
v) other optional ingredients include: a crystal growth inhibitor, preferably HEDP, and glass care agents.

A preferred automatic dishwashing composition of the invention comprises:
i) from 10 to 20% by weight of the composition of bleach, preferably sodium percarbonate;
ii) a manganese bleach catalyst, preferably a bleach catalyst selected from the group consisting of 1,4,7-trimethyl-1,4,7-triazacyclononane (Me-TACN) and 1,2,4,7-tetramethyl-1,4,7-triazacyclononane (Me/Me-TACN), and optionally TAED;
iii) optionally but preferably from 5 to 50% by weight of the composition of sodium carbonate;
iv) optionally but preferably from 1 to 10% by weight of sodium silicate;
v) optionally but preferably from 2 to 10% by weight of the composition of a non-ionic surfactant;
vi) optionally but preferably a glass care agent.

The amylase of the composition of the invention can be used in a laundry detergent.

EXAMPLES

Example 1

AA2560 Variants

Protein Expression, Purification and Quantitation:

AA2560 combinatorial variants in a ΔR181 and ΔG182 (i.e., ΔRG) background were made as synthetic genes and introduced into suitable *Bacillus licheniformis* cells using standard procedures. All mutations were confirmed by DNA sequencing. Cells were grown for 72 hours in a medium suitable for protein expression and secretion in a *B. licheniformis* host. Secreted protein was harvested by centrifugation. Purification was achieved through use of hydrophobic interaction chromatography with Phenyl Sepharose 6 Fast Flow resin (GE Healthcare). Purified proteins were stabilized in a standard formulation buffer containing HEPES as the buffering agent, calcium chloride, and propylene glycol at pH 8. Protein concentration was determined by a mixture of amino acid analysis, high performance liquid chromatography (HPLC) and absorbance at 280 nm.

Enzyme Performance Assay:

The activity of the α-amylase was determined by removal of dyed starch stain from a white melamine tile in a detergent background. Mixed corn/rice colored starch tiles and mixed corn/rice starch tiles with food colorant, purchased from Center for Testmaterials (Catalog Nos. DM277 and DM71), respectively, were used to determine the cleaning activity of the α-amylase. The tiles were affixed to a 96-well plate containing the amylase solution diluted into a working range in an aqueous buffer and added to a pre-made detergent solution of the WFKB detergent (WFK Testgewebe GmbH, Brüggen, Deutschland) such that the total volume was 300 μL. Pre-imaged melamine tiles with colored starch stains were then affixed to the top of the 96 well plate, such that agitation of the assembly leads to splashing of the enzyme containing detergent onto the starch stained surface. The washing reaction was carried out at 50° C. for 15 minutes with shaking at 250 rpm. Following the washing reaction, the melamine tiles were then rinsed briefly under water, dried and re-imaged. The activity of the α-amylases is calculated as the difference in RGB (color) values of the pre and post wash images. The whiter the post wash image, the better the enzyme activity. Performance indices (PI) are calculated as:

$$\frac{\text{change in } RGB \text{ of variant}}{\text{change in } RGB \text{ of wild type}}$$

Performance Indices of Combinatorial Variants Against the ΔRG Variant:

Cleaning performance of the variants in terms of performance index against the wild-type variant are listed in Table 3. A large number of variants were tested. Only data for those with a PI>1 for at least one stain are shown. DM277 is designated stain 1 and DM71 is designated stain 2).

TABLE 1

Variant performance on two different stains

| Mutations | PI-1 | PI-2 |
|---|---|---|
| ΔR181-ΔG182 | -1- | -1- |
| T40N-S91R-Q169H-ΔR181-ΔG182-T183M-H28IN | 1.18 | 1.60 |
| Q172R-ΔR181-ΔG182-E190P-S288D | 1.09 | 1.36 |
| Q172R-ΔR181-ΔG182-S244E-S288D-S474R | 1.15 | 1.82 |
| S91R-Q172R-ΔR181-ΔG182-E190P-I324M | 1.26 | 1.95 |
| T40N-S91R-ΔR181-ΔG182-E190P-F263Y | 1.20 | 1.99 |
| T40N-S91R-ΔR181-ΔG182-S244E-Y364L | 1.20 | 2.19 |
| S91R-Q172R-ΔR181-ΔG182-E190P-I324R | 1.26 | 1.84 |
| S91R-W116R-Q172R-ΔR181-ΔG182-S244E-H281S-S288D | 1.29 | 2.19 |
| T40N-S91R-Y100F-W116R-Q172N-ΔR181-ΔG182-S244Q-H281S | 1.24 | 1.88 |
| T40N-S91R-Q172R-ΔR181-ΔG182-S244Q-F263Y-H281S | 1.19 | 1.94 |
| S91R-Q172R-ΔR181-ΔG182-E190P-1324N | 0.96 | 1.44 |
| T40D-S91R-Q172R-ΔR181-ΔG182-E190P-H281S-I324R | 1.04 | 0.99 |
| ΔR181-ΔG182-Y364L | 2.90 | 2.23 |

All variants in Table 1 perform equal to or better than STAINZYME® Plus 12L (Novozymes) in one or more of the stains and wash conditions tested.

Example 2

Amylase Cleaning Performance in an Automatic Dishwashing

TABLE 1

Automatic Dish Washing (ADW) Compositions
The following ADW composition contains no enzymes.

| Ingredients - (weight grams) | ADW Cleaning Composition |
|---|---|
| Bleach Activator | 0.22 |
| SKS-6 Sodium Disilicate (Na2Si2O5) | 0.8 |

TABLE 1-continued

Automatic Dish Washing (ADW) Compositions
The following ADW composition contains no enzymes.

| Ingredients - (weight grams) | ADW Cleaning Composition |
|---|---|
| HEDP | 0.93 |
| Sodium carbonate | 1.5 |
| MGDA | 7.01 |
| Sulfonic acid group-containing polymer | 0.80 |
| Percarbonate | 3.50 |
| Bleach catalyst | 0.256 |
| Lutensol TO7 | 0.90 |
| Plurafac ® SLF 180 | 0.75 |
| Dipropylene Glycol | 0.40 |
| Minors | balance |
| Total % of full dose | 100 |

Percarbonate
Sulfonic acid group-containing polymer
Bleach catalyst
Bleach Activator
Sodium Percarbonate
Acusol 588
MnTACN (Manganese 1,4,7-Triazacyclononane)
(TAED) Tetraacetylethylenediamine

TABLE 2

Protease and amylase enzyme additions

| Composition A | ADW cleaning composition + 43 mg active Excellase ™ (protease enzyme) + 1.5 mg active Stainzyme ® Plus 12 GT (amylase enzyme) |
|---|---|
| Composition B | ADW cleaning composition + 43 mg active Excellase ™ (protease enzyme) + 1.5 mg active Amylase A of this invention |
| Composition C | ADW cleaning t composition + 43 mg active Excellase ™ (protease enzyme) + 1.5 mg active Amylase B of this invention |
| Composition D | ADW cleaning composition + 43 mg active Excellase ™ (protease enzyme) + 1.5 mg active Amylase C of this invention |

Excellase ™ supplied by DuPont
Stainzyme ® Plus sunnlied by Novozymes

Amylase A is a variant of this invention of the wild type from a *Bacillus* sp., herein, referred to as AA2560 SEQ ID NO: 1: with the following two deletions at positions 181-182 and including the following substitutions; T40N-S91R-Y100F-W116R-Q172N-S244Q-H281S Amylase B is a variant of this invention of the wild type from a *Bacillus* sp., herein, referred to as AA2560 SEQ ID NO: 1: with the following two deletions at positions 181-182 and including the following substitutions; T40N-S91R-Q172N-S244Q-F263Y-H281S Amylase C is a variant of this invention of the wild type from a *Bacillus* sp., herein, referred to as AA2560 SEQ ID NO: 1: with the following two deletions at positions 181-182 and including the following substitution; Y364L Cleaning Performance Method: Mixed Amylase Cleaning Using a Miele Model GSL2

The automatic dishwashing (ADW) cleaning performance of ADW composition as described in Tables 1 and 2 was evaluated, measured by the cleaning performance on mixed starch tiles (DM71, DM376, DM377, DM378) supplied by Center For Testmaterials BV. Stoomloggerweg 11, 3133 KT Vlaardingen, the Netherlands. One dose of detergent composition 17.32 g (combined solid and liquid components) and enzyme additions described in Table 2 were added to each automatic dishwasher at the opening of the dispenser drawer of each cycle.

In a Miele automatic dishwasher; model GSL2, mixed starch CFT tiles were washed at 45° C., (8 min holding time, 55° C. rinse), 21 gpg water hardness. Ballast soil was added as a mixed soil composition to each treatment as described in Table 3. The CFT Tiles were added to the machine (2 internal replicates of each tile) before closing the machine door. The machine was then started, as the dispenser drawer opened, the cleaning composition including the enzyme additions were dosed to each machine along with a 50 g mixed soil pot. This was repeated a further three times to result in four external replicates per treatment.

TABLE 3

Ballast soil - mixed soil composition

| Ingredients | Raw Material | % Composition |
|---|---|---|
| Fat Components | | |
| | Vegetable Oil | 31.6 |
| | Margarine | 6.3 |
| | Lard | 6.3 |
| | Deep Frying Fat | 6.3 |
| Protein | | |
| | Whole Egg | 15.8 |
| | Cream (32% fat) | 9.4 |
| | Whole Milk Pasteurized (3.5% fat) | 6.3 |
| Powdered Solid | | |
| | Potato Starch | 2.2 |
| | Gravy | 1.7 |
| | Wheat flour | 0.6 |
| | Quark powder | 0.6 |
| | Benzoic acid >99.9% active | 0.3 |
| Other | | |
| | Tomato Ketchup | 3.6 |
| | Mustard | 6.3 |
| Total | | 100 |

Soil Preparation following IKW Standardized protocol:
1. Combine the vegetable oil and whole egg and mix thoroughly for 30 minutes.
2. Add the ketchup and mustard, continue to stir vigorously.
3. Melt the fats, allow to cool to 40° C., then add to the mixture and blend in well.
4. Stir in the cream and milk.
5. Add the powdered solid constituents and mix everything to a smooth paste.
6. Finally, put 50 g of the soil mix into separate plastic beakers.
Freeze the beakers of soil until required for use.

Four External replicates were carried out as measured by the four starch stains included and the removal performance for each test composition was calculated (eight replicates were generated from the inclusion of four external and two internal replicates for each treatment). The cleaning performance of Composition A (containing Excellase™ and Stainzyme® Plus) was taken as reference as compared to Composition B (containing Excellase™ and Amylase A of this invention), Composition C (containing Excellase™ and Amylase B of this invention) and Composition D (containing Excellase™ and Amylase C of this invention). The stains were analysed using image analysis, with results presented below calculated as percentage stain removal whereby; 0=no removal, 100=complete removal. I.e. Stain Removal Index (SRI).

The results shown in Table 4 below are expressed as stain removal indices.

TABLE 4

Cleaning performance of Composition A vs Compositions B, C and D on mixed starch stains

| Cleaning performance (SRI) | Detergent Composition A | Detergent Composition B | Detergent Composition C | Detergent Composition D |
|---|---|---|---|---|
| DM71 Starch with Colorant | 30.9 | *49.8 | *52.3 | *56.9 |
| DM376 Triple Corn Starch | 45.9 | *84.9 | *85.3 | *82.6 |
| DM377 Triple Mixed Starch | 43.4 | *79.2 | *78.6 | *74.7 |
| DM378 Triple Rice Starch | 53.1 | *74.7 | *76.2 | *66.5 |

*Statistical evaluation of the data shows a significant difference at 95% confidence between detergent Composition A and Compositions B, C and D Starch cleaning is a measure of the ADW cleaning after washing. As can be seen from the results Table 4 above, the starch removal is significantly improved for Composition B comprising Amylase A of this invention, Composition C comprising Amylase B of this invention and Composition D comprising Amylase C of this invention, vs. Composition A comprising Stainzyme® Plus 12 GT. It can be concluded that each amylase of this invention described as Amylase B, C and D provide significantly improved starch cleaning performance vs Stainzyme® Plus contained in Composition A.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An automatic dishwashing cleaning composition comprising a variant α-amylase,
wherein the variant α-amylase comprises amino acid substitution(s) selected from the group consisting of: a substitution at the position corresponding to position 91 of SEQ ID NO: 1 and a substitution at the position corresponding to position 40 of SEQ ID NO: 1,
wherein the variant α-amylase has α-amylase activity, and the amino acid sequence of the variant α-amylase has at least 95% amino acid sequence identity to the amino acid sequence of SEQ ID NO: 1; and
wherein the variant α-amylase comprises:
(i) substitutions selected from the group consisting of:
(a) X40N-X91R-X169H-X183M-X281N,
(b) X91R-X172R-X190P-X324M,
(c) X40N-X91R-X190P-X263Y,
(d) X40N-X91R-X244E-X364L,
(e) X91R-X172R-X190P-X324R,
(f) X91R-X116R-X172R-X244E-X281S-X288D,
(g) X40N-X91R-X100F-X116R-X172N-X244Q-X281S,
(h) X40N-X91R-X172R-X244Q-X263Y-X281S,
(i) X91R-X172R-X190P-X324N, and
(j) X40D-X91R-X172R-X190P-X281S-X324R; and
(ii) pairwise deletions of residues selected from the group consisting of:
residues 181 and 182, and
residues 183 and 184,
wherein amino acid position numbering is relative to the amino acid sequence of SEQ ID NO: 1.

2. The composition according to claim 1, wherein the substitution at the position corresponding to position 91 is S91R.

3. The composition according to claim 1, wherein the substitution at the position corresponding to position 40 is X40N.

4. The composition according to claim 1, wherein the substitution at the position corresponding to position 40 is selected from the group consisting of T40N and T40D.

5. The composition according to claim 1, wherein the variant α-amylase further comprises a mutation at the position corresponding to position 172 of SEQ ID NO: 1.

6. The composition according to claim 5, wherein the mutation at the position corresponding to position 172 of SEQ ID NO: 1 is a substitution with R or N.

7. The composition according to claim 1, wherein the variant α-amylase further comprises mutations at the positions corresponding to positions 172 and 288 of SEQ ID NO: 1.

8. The composition according to claim 6, wherein the variant α-amylase further comprises mutations at the positions corresponding to positions 116 and 281 of SEQ ID NO: 1.

9. The composition according to claim 1, wherein the variant α-amylase further comprises mutation(s) at the position corresponding to position 190 and/or 244 of SEQ ID NO: 1.

10. The composition according to claim 1, wherein the variant α-amylase comprises pairwise deletion of residues 181 and 182.

11. The composition according to claim 1, wherein the variant α-amylase comprises:
pairwise deletions of residues selected from the group consisting of:
R181 and G182, and
T183 and G184.

12. The composition according to claim 1, wherein the variant α-amylase comprises the following features:
(a) D or N at position 40 and/or R at position 91,
(b) N or R at position 172, and
(c) pairwise deletions at positions 181 and 182.

13. The composition according to claim 1, further comprising a protease, wherein the amino acid sequence of the protease has at least 80% amino acid sequence identity with the amino acid sequence of SEQ ID NO: 5 or with the amino acid sequence of SEQ ID NO: 6, and wherein the protease comprises amino acid substitutions selected from the group consisting of:
(i) X198G/A/K/L/Q/R/T/V/S/L, X207Q, X211Q/N and X212Q in combination with at least three amino acid substitutions selected from the group consisting of: X039E, X074D, X099R, X126A, X127E and X128G;
(ii) X039E-X074D-X099R-X116R-X126A-X127E-X128G-X211Q;
(iii) X039E-X074D-X099R-X126A-X127E-X128G-X211N;
(iv) X039E-X074D-X099R-X126A-X127E-X128G-X211Q;
(v) X039E-X074D-X099R-X126A-X127E-X128G-X207Q;
(vi) any one of the proteases of (i), (ii), (iii), (iv), or (v) further comprising at least one amino acid substitution selected from X242D and X256E; and
(vii) X039E-X074D-X099R-X126A-X127E-X128G-X256E;
wherein amino acid position numbering is relative to the amino acid sequence of SEQ ID NO: 6.

14. The composition according to claim 1, further comprising a protease, wherein the amino acid sequence of the protease has at least 90% amino acid sequence identity with the amino acid sequence of SEQ ID NO: 6, and wherein the protease comprises one or more, or two or more or three or more amino acid mutations selected from the group consisting of:
S3V, S9R, A13V, A11ST, G20*, L21F, I35V, N60D, V66A, N74D, S85N/R, S97SE, S97AD, S97D/G, S99G/M/D/E, S101A, V102E/I, G116V/R, S126F/L, P127Q, S128A, S154D, G157S, Y161A, R164S, A188P, V199I, Q200C/E/I/K/T/V/W/L, Y203W, N212D, M216S/F, A222V, Q239R/F, T249R, N255D, and L256E,N,Q,D.

15. The composition according to claim 1, further comprising:
from 10% to 50% by weight of the composition of an organic complexing agent system; and
more than 10% by weight of the composition of a bleaching system, wherein the bleaching system comprises bleach and at least one of a bleach activator and a bleach catalyst.

16. The composition according to claim 1, further comprising a bleach catalyst, wherein the bleach catalyst is a manganese bleach catalyst selected from the group consisting of 1,4,7-trimethyl-1,4,7-triazacyclononane (Me-TACN), 1,2,4,7-tetramethyl-1,4,7-triazacyclononane (Me/Me-TACN), and mixtures thereof.

17. A method of washing soiled dishware in a dishwasher comprising the steps of:
i) providing the soiled dishware;
ii) using a long hot program, having a main wash cycle lasting more than 15 minutes at a temperature of at least 40° C.;
iii) treating the soiled dishware with the cleaning composition according to claim 1 resulting in treated dishware; and
iv) rinsing the treated dishware.

18. An automatic dishwashing cleaning composition comprising:
a variant α-amylase, wherein the variant α-amylase comprises amino acid substitution(s) selected from the group consisting of:
a substitution at the position corresponding to position 91 of SEQ ID NO: 1 and a substitution at the position corresponding to position 40 of SEQ ID NO: 1,
wherein the variant α-amylase has α-amylase activity, and the amino acid sequence of the variant α-amylase has at least 95% amino acid sequence identity to the amino acid sequence of SEQ ID NO: 1
wherein amino acid position numbering of the variant α-amylase is relative to the amino acid sequence of SEQ ID NO: 1; and
a protease, wherein the amino acid sequence of the protease has at least 80% amino acid sequence identity with the amino acid sequence of SEQ ID NO: 5 or with the amino acid sequence of SEQ ID NO: 6 and wherein the protease comprises amino acid substitutions selected from the group consisting of:
(i) X198G/A/K/L/Q/R/T/V/S/L, X207Q, X211Q/N and X212Q in combination with at least three amino acid substitutions selected from the group consisting of: X039E, X074D, X099R, X126A, X127E and X128G;
(ii) X039E-X074D-X099R-X116R-X126A-X127E-X128G-X211Q;
(iii) X039E-X074D-X099R-X126A-X127E-X128G-X211N;
(iv) X039E-X074D-X099R-X126A-X127E-X128G-X211Q;

(v) X039E-X074D-X099R-X126A-X127E-X128G-X207Q;

(vi) any one of the proteases of (i), (ii), (iii), (iv), or (v) further comprising at least one amino acid substitution selected from X242D and X256E; and (vii) X039E-X074D-X099R-X126A-X127E-X128G-X256E;

wherein amino acid position numbering of the protease is relative to the amino acid sequence of SEQ ID NO: 6.

19. An automatic dishwashing cleaning composition comprising a variant α-amylase, wherein the variant α-amylase comprises amino acid substitution(s) selected from the group consisting of: a substitution at the position corresponding to position 91 of SEQ ID NO: 1 and a substitution at the position corresponding to position 40 of SEQ ID NO: 1, wherein the variant α-amylase has α-amylase activity, and the amino acid sequence of the variant α-amylase has at least 95% amino acid sequence identity to the amino acid sequence of SEQ ID NO: 1; and wherein the variant α-amylase comprises the following features:

(a) D or N at position 40 and/or R at position 91, (b) N or R at position 172, and (c) pairwise deletions at positions 181 and 182, wherein amino acid position numbering is relative to the amino acid sequence of SEQ ID NO: 1.

20. The composition according to claim 19, further comprising a protease, wherein the amino acid sequence of the protease has at least 80% amino acid sequence identity with the amino acid sequence of SEQ ID NO: 5 or with the amino acid sequence of SEQ ID NO: 6 and wherein the protease comprises amino acid substitutions selected from the group consisting of:

(i) X198G/A/K/L/Q/R/T/V/S/L, X207Q, X211Q/N and X212Q in combination with at least three amino acid substitutions selected from the group consisting of: X039E, X074D, X099R, X126A, X127E and X128G;

(ii) X039E-X074D-X099R-X116R-X126A-X127E-X128G-X211Q;

(iii) X039E-X074D-X099R-X126A-X127E-X128G-X211N;

(iv) X039E-X074D-X099R-X126A-X127E-X128G-X211Q;

(v) X039E-X074D-X099R-X126A-X127E-X128G-X207Q;

(vi) any one of the proteases of (i), (ii), (iii), (iv), or (v) further comprising at least one amino acid substitution selected from X242D and X256E; and (vii) X039E-X074D-X099R-X126A-X127E-X128G-X256E;

wherein amino acid position numbering is relative to the amino acid sequence of SEQ ID NO: 6.

\* \* \* \* \*